United States Patent
Wong et al.

(10) Patent No.: US 7,396,817 B2
(45) Date of Patent: Jul. 8, 2008

(54) BIOLOGICALLY ACTIVE PEPTIDES COMPRISING ISOLEUCYL-VALYL-THREONYL-ASPARAGINYL-THREONYL-THREONINE (IVTNTT)

(75) Inventors: Wai Ming Wong, Hong Kong (CN); Kong Lam, Shenzhen (CN)

(73) Assignee: CMS Peptides Patent Holding Company Limited, Tortola (VG)

( * ) Notice: Subject to any disclaimer, the term of this patent is extended or adjusted under 35 U.S.C. 154(b) by 121 days.

(21) Appl. No.: 10/595,842

(22) PCT Filed: Nov. 18, 2004

(86) PCT No.: PCT/GB2004/004877

§ 371 (c)(1),
(2), (4) Date: May 16, 2006

(87) PCT Pub. No.: WO2005/051981

PCT Pub. Date: Jun. 9, 2005

(65) Prior Publication Data

US 2006/0234943 A1    Oct. 19, 2006

Related U.S. Application Data

(60) Provisional application No. 60/523,837, filed on Nov. 19, 2003.

(51) Int. Cl.
*A61K 38/08* (2006.01)
*C07K 7/06* (2006.01)

(52) U.S. Cl. .......................................... 514/17; 530/329
(58) Field of Classification Search ................... None
See application file for complete search history.

(56) References Cited

FOREIGN PATENT DOCUMENTS

WO        WO 0175067 A2    11/2001

OTHER PUBLICATIONS

Bouchonnet et al. Fragmentations of Dipeptides in Plasma Desorption Mass Spectrometry . . . Biological Mass Spectrometry. 1992, vol. 21, pp. 576-584.*
Vassilev Milen et al. "Effect of low molecular weight glycoproteins in chronic hepatitis B" Hepato-Gastroenterology, vol. 43, No. 10, 1996, p. 882-886.
Database Geneseq, Feb. 13, 2002 retrieved from EBI, accession no. ABG03266, SEQ ID No. 33625 SEQ ID No. 33625 of WO0175067.

* cited by examiner

*Primary Examiner*—Jeffrey E Russel
(74) *Attorney, Agent, or Firm*—Eagle IP Limited; Jacqueline C. Lui

(57) ABSTRACT

The peptide Isoleucyl-valyl-threonyl-asparaginyl-threonyl-threonine (SEQ ID NO.1) is disclosed with its use as a pharmaceutical composition in reducing symptoms of viral disease and stimulating properties of immune system in a subject. A method is also disclosed for making a pharmaceutical composition comprising providing an Isoleucyl-valyl-threonyl-asparaginyl-threonyl-threonine (SEQ ID NO.1) peptide and mixing said peptide with a pharmaceutical acceptable carrier.

14 Claims, 5 Drawing Sheets

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: Synthetic Peptide

<400> SEQUENCE: 1

Ile Val Thr Asn Thr Thr
1               5
```

BIOLOGICALLY ACTIVE PEPTIDES COMPRISING ISOLEUCYL-VALYL-THREONYL-ASPARAGINYL-THREONYL-THREONINE (IVTNTT)

CROSS-REFERENCE TO RELATED APPLICATIONS

This Application claims the benefit of provisional application Ser. No. 60/523,837 filed on 19 Nov., 2003, under 35 U.S.C. § 119(E).

BACKGROUND OF THE INVENTION

1. Field of the Invention

The present invention is related to short peptides and the use thereof. In particular, the present invention is related to short peptides with biological activities.

The hard copy of the substitute sequence listing and the substitute computer readable form submitted on Feb. 5, 2008 are both incorporated herein by reference in their entireties.

2. Description of the Related Art

Peptides are known in the art for treatment of diseases and as pharmaceutical compositions. For example, U.S. Pat. No. 6,191,113 discloses a peptide that has inhibitory activity for the growth of smooth muscle cells and is therefore useful for preventing and treating pathological conditions associated with growth of smooth muscle cells such as arteriosclerosis, restenosis after angioplasty, luminal stenosis after grafting blood vessel and smooth muscle sarcoma. U.S. Pat. No. 6,184,208 discloses another peptide that is found to modulate physiological processes such as weight gain activity of the epithelial growth zone and hair growth. Furthermore, PCT publication no. WO 03/006492 and U.S. patent application Ser. No. 10/237,405 suggested that certain peptides and their pharmaceutical compositions are biologically active and capable of modulating immune responses.

It is therefore an object of the present invention to provide a short peptide or peptides that have biological activity.

SUMMARY OF THE INVENTION

One aspect of the present invention relates to the hexapeptide CMS017, Isoleucyl-valyl-threonyl-asparaginyl-threonyl-threonine (IVTNTT) (SEQ ID NO:1), which has been found to contain biological activity. For testing purposes, the peptide L-Isoleucyl-L-valyl-L-threonyl-L-asparaginyl-L-threonyl-L-threonine has been used. Further aspects of the present invention include an isolated or purified peptide comprising, consisting essentially of, or consisting of Isoleucyl-valyl-threonyl-asparaginyl-threonyl-threonine (SEQ ID NO: 1). Another aspect relates to substantially pure IVTNTT (CMS017) (SEQ ID NO:1) peptides.

An additional aspect of the present invention comprises an isolated or purified peptide consisting essentially of the peptide IVTNTT (CMS017) (SEQ ID NO:1). In one specific embodiment, the peptide has immuno-regulatory and anti-viral activity.

Additional aspects of the present invention include pharmaceutical compositions comprising, consisting essentially of, or consisting of the peptide IVTNTT (CMS017) (SEQ ID NO:1). Other aspects of the present invention relate to pharmaceutical compositions that comprise, consist essentially of or consist of a functional derivative of the IVTNTT (CMS017) (SEQ ID NO:1).

Another aspect of the present invention relates to a method of making a pharmaceutical composition comprising providing the peptide IVTNTT (CMS017) (SEQ ID NO:1) and mixing said peptide with a pharmaceutical acceptable carrier.

Another aspect of the present invention relates to a method of reducing the effects of immuno-suppression or viral disease comprising administering a pharmaceutically effective dose the peptide IVTNTT (CMS017) (SEQ ID NO:1) to a human. In additional aspects of the present invention, the viral disease is hepatitis B infection.

Another aspect of the present invention relates to the use of the peptide IVTNTT (CMS017) (SEQ ID NO:1) as a pharmaceutical composition. Furthermore, the hexapeptide may be used to treat a immunological disorder or viral disease. In some particular aspects of the invention, a hepatitis B infection is treated.

A further aspect of the present invention is directed to a nutritional composition containing the peptide IVTNTT (CMS017) (SEQ ID NO:1) and the use of the same for the manufacture of a nutritional supplement.

In a further aspect of the present invention, enhanced derivatives of the CMS017 peptide (IVTNTT) (SEQ ID NO:1) and functional derivatives thereof are provided. Enhanced derivatives of the peptide IVTNTT (CMS017) (SEQ ID NO:1) comprise an enhancement molecule operably linked to the peptide IVTNTT (CMS017) (SEQ ID NO:1) in such a manner as to improve or augment the therapeutic effectiveness of the peptide. The enhancement effect may be that of a prolonged effect, a shortened effect, a delayed onset of effect, a hastened onset of effect, an increased intensity of effect, a decreased intensity of effect, a reduction in side effects, the creation of one or more effects, a delayed subsiding of effect, a hastened subsiding of effect and a targeting of the peptide to a discrete location within an individual. Examples of such enhancement molecules and enhanced derivatives are described below. In some aspects of the invention, the enhanced molecules can treat or prevent, but are not limited to treating or preventing, viral infections and immunological disorders. Additional aspects of the present invention include methods of enhancing the therapeutic effects of a peptide comprising, consisting essentially of or consisting of a peptide selected from the group consisting of IVTNTT (CMS017) (SEQ ID NO:1) and its derivatives, comprising operably linking said peptide to a molecule which enhances the therapeutic effect. In some aspects of the invention, said operably linked molecule which enhances the therapeutic effect is not a peptide that is adjacent to a peptide selected from the group consisting of IVTNTT (CMS017) (SEQ ID NO:1) and its derivatives in a naturally occurring peptide. Additional aspects of the present invention include pharmaceutical compositions comprising, consisting essentially of or consisting of enhanced derivatives of a peptide selected from the group consisting of IVTNTT (CMS017) (SEQ ID NO:1) and its functional derivatives.

One aspect of the present invention relates to a substantially pure peptide selected from the group consisting of IVTNTT (CMS017) (SEQ ID NO:1) and its functional derivatives disclosed above operably linked to a molecule that enhances their therapeutic effectiveness, also known herein as "enhancement molecules". Such molecules may be prepared and used in any of the ways described in U.S. Provisional Patent Application No. 60/435,796, entitled "Biologically active peptide conjugates", and filed on Dec. 18, 2002, the disclosure of which is incorporated herein by reference in its entirety. Candidate molecules to be operably linked to the peptides and the means for carrying out such linkings are familiar to those with skill in the art. Some molecules that could be operably linked to a peptide selected from the group consisting of IVTNTT (CMS017) (SEQ ID NO:1) and its functional derivatives include, but are not limited to, an organic compound, a carbohydrate, a sugar, a polysaccharide, an amino acid, an amino acid polymer, a peptide, a steroid, a protein, an isolated domain of a protein, a hapten, an antigen, a lipid molecule, a fatty acid, a bile acid, a polyamine, a protease inhibitor, a silicate and a combination of any of the preceding molecules. The invention also relates to a substantially pure peptide selected from the group consisting of IVT-NTT (CMS017) (SEQ ID NO:1) disclosed above and functional derivatives thereof operably linked to a molecule that enhances its therapeutic effectiveness, wherein said operably linked molecule is not a peptide which is adjacent to the above-disclosed peptide in a naturally occurring peptide. In another aspect of the invention, a substantially pure peptide selected from the group consisting of IVTNTT (CMS017) (SEQ ID NO:1) and functional derivatives thereof can treat and/or prevent, but are not limited to treating and/or preventing, immunological disorders or viral infections, such as hepatitis B infection. The molecule may be operably linked to the peptide of the invention with a covalent bond or a non-covalent interaction.

In specific embodiments, biologically effective molecules, when operably linked to a peptide selected from the group consisting of IVTNTT (CMS017) (SEQ ID NO:1) and functional derivatives thereof, can alter the pharmacokinetics of the peptide by conferring properties to the peptide as part of a linked molecule. Some of the properties that the operably linked molecules can confer on peptides include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect.

Another aspect of the present invention relates to substantially pure peptides comprising, consisting essentially of or consisting of a peptide selected from the group consisting of IVTNTT (CMS017) (SEQ ID NO:1) and functional derivatives thereof operably linked to a molecule which enhances its therapeutic effectiveness, wherein said operably linked molecule is not a peptide which is adjacent to a peptide selected from the group consisting of IVTNTT (CMS017) (SEQ ID NO:1) and its derivatives in a naturally occurring peptide. Some molecules that could be operably linked a peptide selected from the group consisting of IVTNTT (CMS017) (SEQ ID NO:1) and functional derivatives thereof include, but are not limited to, an organic compound, a carbohydrate, a sugar, a polysaccharide, an amino acid, an amino acid polymer, a peptide, a steroid, a protein, an isolated domain of a protein, a hapten, an antigen, a lipid molecule, a fatty acid, a bile acid, a polyamine, a protease inhibitor, a silicate and a combination of any of the preceding molecules. Additional aspects of the invention include substantially pure peptides comprising, consisting essentially of or consisting of a peptide selected from the group consisting of IVTNTT (CMS017) (SEQ ID NO:1) and functional derivatives thereof operably linked to a molecule which enhances its therapeutic effectiveness that can treat and/or prevent, but are not limited to treating and/or preventing, immunological disorders or viral infections, such as hepatitis B infections. The molecule may be operably linked to the peptide of the invention with a covalent bond or a non-covalent interaction. The effects of the operable linkage between the substantially pure peptides and the molecule which enhances its therapeutic effectiveness can include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect.

Another aspect of the present invention relates to hybrid peptides containing the peptide comprising a peptide selected from the group consisting of IVTNTT (CMS017) (SEQ ID NO:1) and functional derivatives thereof with an additional peptide sequence attached, where said attached additional sequence is not a sequence found adjacent to the peptide disclosed above in a naturally occurring peptide. In specific embodiments, the hybrid peptides above can treat and/or prevent, but are not limited to treating and/or preventing, immunological disorders or viral infections such as hepatitis B infections. In specific embodiments, these attached additional peptide sequences, not found adjacent to a peptide selected from the group consisting of IVTNTT (CMS017) (SEQ ID NO:1) and its derivatives in a naturally occurring peptide, can alter the pharmacokinetics of the peptides of the above described embodiments of the invention by virtue of conferring properties to the peptide as part of a hybrid molecule. Some of the properties that the operably linked molecules can confer on a peptide selected from the group consisting of IVTNTT (CMS017) (SEQ ID NO:1) and functional derivatives thereof include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect.

Another aspect of the present invention relates to a genetic vector comprising, consisting essentially of, or consisting of a first nucleotide sequence encoding a peptide selected from the group consisting of IVTNTT (CMS017) (SEQ ID NO:1) and functional derivatives thereof fused in frame with a second nucleotide sequence encoding a peptide that enhances the therapeutic effectiveness of the aforementioned peptide and that is not adjacent to said peptide selected from the group consisting of IVTNTT (CMS017) (SEQ ID NO:1) or its functional derivatives thereof in a naturally occurring peptide. It also relates to a genetic vector comprising, consisting essentially of, or consisting of a first nucleotide sequence encoding a peptide consisting essentially of a peptide selected from the group consisting of IVTNTT (CMS017) (SEQ ID NO:1) and functional derivatives thereof fused in frame with a second nucleotide sequence encoding a peptide that enhances the therapeutic effectiveness of the aforementioned peptide and that is not adjacent to said peptide selected from the group consisting of IVTNTT (CMS017) (SEQ ID NO:1) or its functional derivatives thereof in a naturally occurring peptide. It further relates to a genetic vector comprising, consisting essentially of, or consisting of a first nucleotide sequence encoding a peptide consisting of the amino acid sequence of a peptide selected from the group consisting of IVTNTT (CMS017) (SEQ ID NO:1) and functional derivatives thereof fused in frame with a second nucleotide sequence encoding a peptide that enhances the therapeutic effectiveness of the aforementioned peptide and that is not adjacent to said peptide selected from the group consisting of IVTNTT (CMS017) (SEQ ID NO:1) and functional derivatives thereof in a naturally occurring peptide. In specific embodiments, said peptide selected from the group consisting of IVTNTT (CMS017) (SEQ ID NO:1) and functional derivatives thereof can treat and/or prevent, but are not limited to treating and/or preventing, immunological disorders or viral infections, such as hepatitis B infections. Some of the properties that the operably linked molecules can confer on said peptide selected from the group consisting of IVTNTT (CMS017) (SEQ ID NO:1) and functional derivatives thereof include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect. Another aspect of the invention relates to micro-organisms that comprise nucleic acid sequences selected from the list consisting of: the nucleotide sequences of the vectors described above; and a nucleotide sequence comprising a first nucleotide sequence encoding a peptide comprising an amino acid sequence of a peptide selected from the group consisting of IVTNTT (CMS017) (SEQ ID NO:1) and functional derivatives thereof fused in frame with a second nucleotide sequence encoding a peptide that is not adjacent to said peptide selected from the group consisting of IVTNTT (CMS017) (SEQ ID NO:1) and functional derivatives thereof in a naturally occurring peptide.

In connection with any of the above-described nucleic acid sequences, the peptides and/or hybrid peptides expressed from these nucleic acid sequences can treat and/or prevent, but are not limited to treating and/or preventing, immunological disorders or viral diseases, such as hepatitis B infection.

A further aspect of the present invention relates to a method of making a pharmaceutical composition comprising providing a peptide selected from the group consisting of IVTNTT (CMS017) (SEQ ID NO:1) and functional derivatives thereof operably linked to a molecule which enhances its therapeutic effect; and formulating said peptide operably linked with said molecule with a pharmaceutically acceptable carrier. The invention also relates to said method wherein said peptide can treat and/or prevent, but are not limited to treating and/or preventing, immunological disorders or viral diseases, such as hepatitis B infection. Some examples of biologically effective molecules that could be attached to said peptide selected from the group consisting of IVTNTT (CMS017) (SEQ ID NO:1) and functional derivatives thereof include, but are not limited to, an organic compound, a carbohydrate, a sugar, a polysaccharide, an amino acid, an amino acid polymer, a peptide, a steroid, a protein, an isolated domain of a protein, a hapten, an antigen, a lipid molecule, a fatty acid, a bile acid, a polyamine, a protease inhibitor, a silicate and a combination of any of the preceding molecules. The invention also relates to a method of making of pharmaceutical comprising a peptide comprising said peptide selected from the group consisting of IVTNTT (CMS017) (SEQ ID NO:1) and functional derivatives thereof comprising operably linking said peptide to a molecule which enhances said therapeutic effect, wherein said molecule is not a peptide which is adjacent to said peptide selected from the group consisting of IVTNTT (CMS017) (SEQ ID NO:1) and functional derivatives thereof in a naturally occurring peptide. The molecule may be operably linked to a peptide of the invention with a covalent bond or a non-covalent interaction. In a specific embodiment, the properties that said linked molecule can confer on said peptides to enhance their therapeutic effects include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect. It also relates to a method of making a pharmaceutical composition comprising providing a substantially pure peptide consisting essentially of the amino acid sequence of a peptide selected from the group consisting of IVTNTT (CMS017) (SEQ ID NO:1) and functional derivatives thereof operably linked to a molecule which enhances its therapeutic effect; and formulating said peptide operably linked with said molecule with a pharmaceutically acceptable carrier. It further relates to a method of making a pharmaceutical composition comprising providing a substantially pure peptide consisting of a peptide selected from the group consisting of IVTNTT (CMS017) (SEQ ID NO:1) and functional derivatives thereof operably linked to a molecule which enhances its therapeutic effect; and formulating said peptide operably linked with said molecule with a pharmaceutically acceptable carrier.

Yet a further aspect of the present invention relates to a method of treatment of a human comprising administering a pharmaceutically effective dose of a substantially pure peptide selected from the group consisting of IVTNTT (CMS017) (SEQ ID NO:1) and functional derivatives thereof to a human, said peptide being operably linked to a molecule which enhances its therapeutic effectiveness. Some examples of biologically effective molecules that could be operably linked to said peptide selected from the group consisting of IVTNTT (CMS017) (SEQ ID NO:1) and functional derivatives thereof include, but are not limited to, an organic compound, a carbohydrate, a sugar, a polysaccharide, an amino acid, an amino acid polymer, a peptide, a steroid, a protein, an isolated domain of a protein, a hapten, an antigen, a lipid molecule, a fatty acid, a bile acid, a polyamine, a protease inhibitor, a silicate and a combination of any of the preceding molecules. In some embodiments, the properties that said operably linked molecule can confer on said peptides to enhance their therapeutic effects include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect.

In particular embodiments, the peptides used for the treatment of human described above may be used to treat and/or prevent, but are not limited to treating and/or preventing, immunological disorders or viral diseases, such as hepatitis B infection.

Further aspects of the invention include pharmaceutical compositions comprising, consisting essentially of, or consisting of a peptide selected from the group consisting of IVTNTT (CMS017) (SEQ ID NO:1) and functional derivatives thereof operably linked to a molecule which enhances its therapeutic effect and a pharmaceutically acceptable carrier. The invention also relates to said enhanced peptide selected from the group consisting of IVTNTT (CMS017) (SEQ ID NO:1) and functional derivatives thereof where the peptide can treat and/or prevent, but are not limited to treating and/or preventing, immunological disorders or viral diseases, such as hepatitis B infection. Some examples of biologically effective molecules that could be operably linked to said peptide selected from the group consisting of IVTNTT (CMS017) (SEQ ID NO:1) and functional derivatives thereof include, but are not limited to, an organic compound, a carbohydrate, a sugar, a polysaccharide, an amino acid, an amino acid polymer, a peptide, a steroid, a protein, an isolated domain of a protein, a hapten, an antigen, a lipid molecule, a fatty acid, a bile acid, a polyamine, a protease inhibitor, a silicate and a combination of any of the preceding molecules. In some embodiments, the properties that said operably linked molecule can confer on said peptides to enhance their therapeutic effects include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect.

BRIEF DESCRIPTION OF THE DRAWINGS

Each of the five figures demonstrates exemplary chemical reactions for linking peptides to steroid molecules.

DETAILED DESCRIPTION OF THE PREFERRED EMBODIMENT

Figure 1:
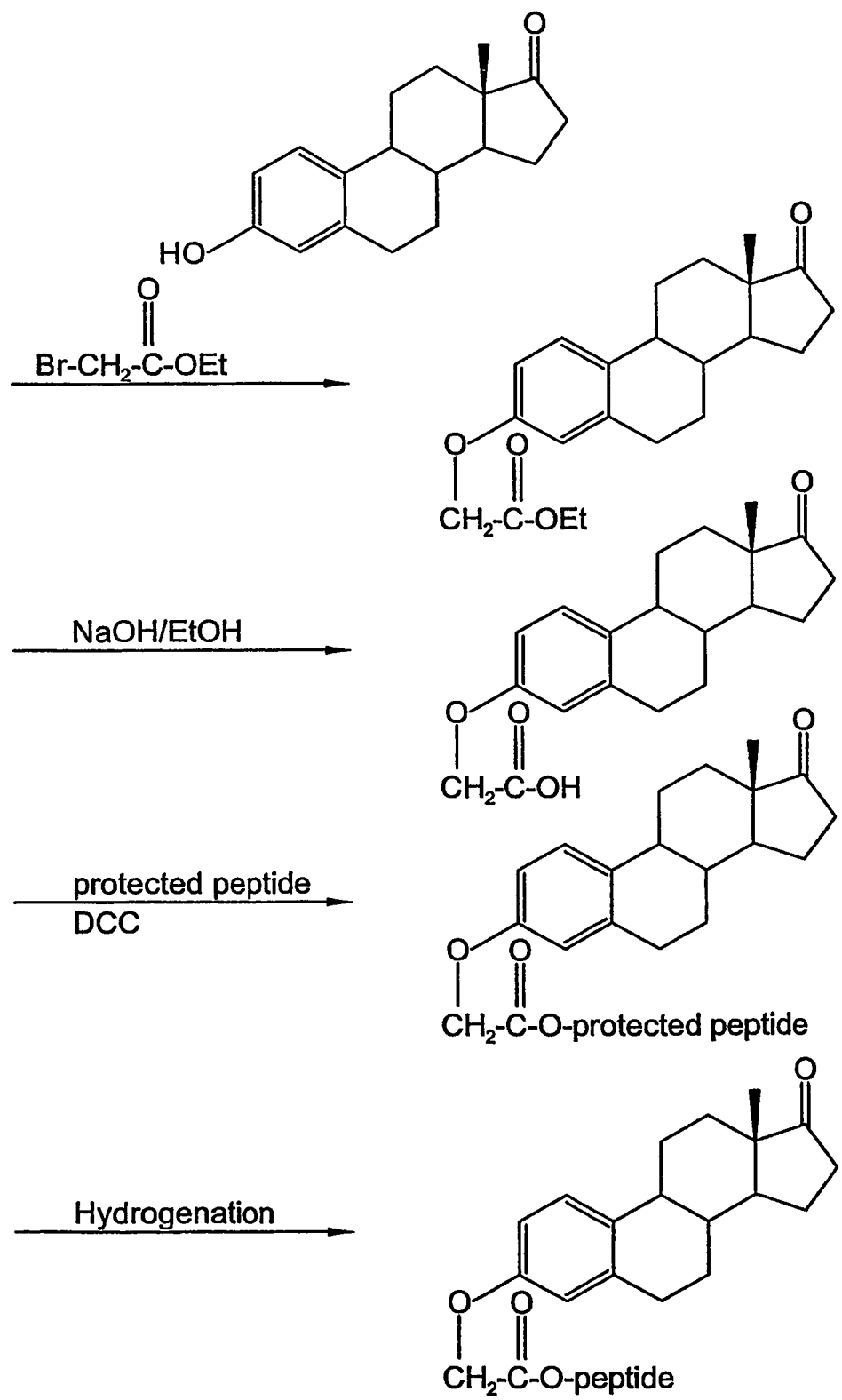
FIG. 1 shows a series of chemical reactions for linking a peptide to an estrone molecule with a covalent bond.
Figure 2:
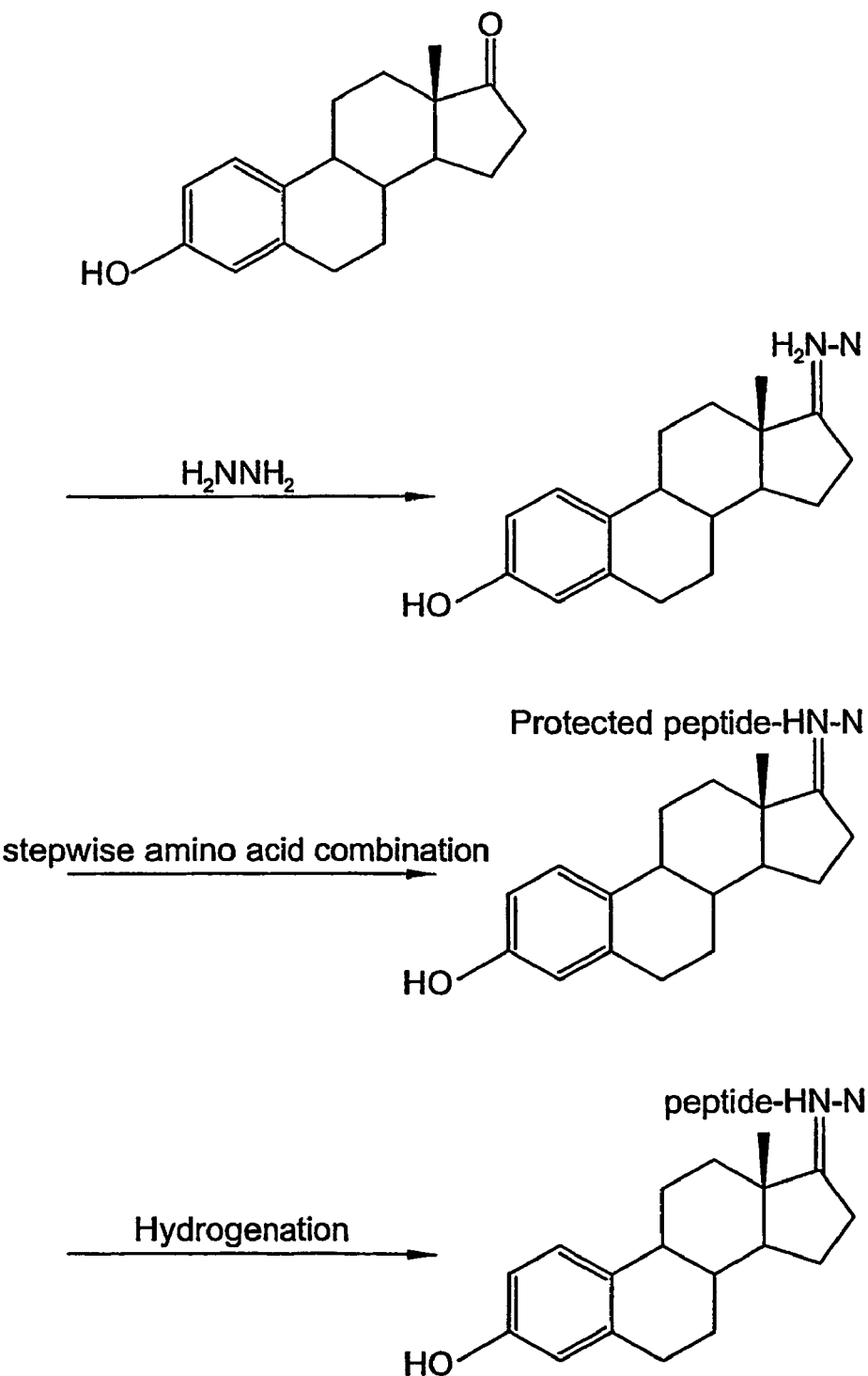
FIG. 2 shows a second, alternative set of reactions for creating the same linkage as in FIG. 1.
Figure 3:
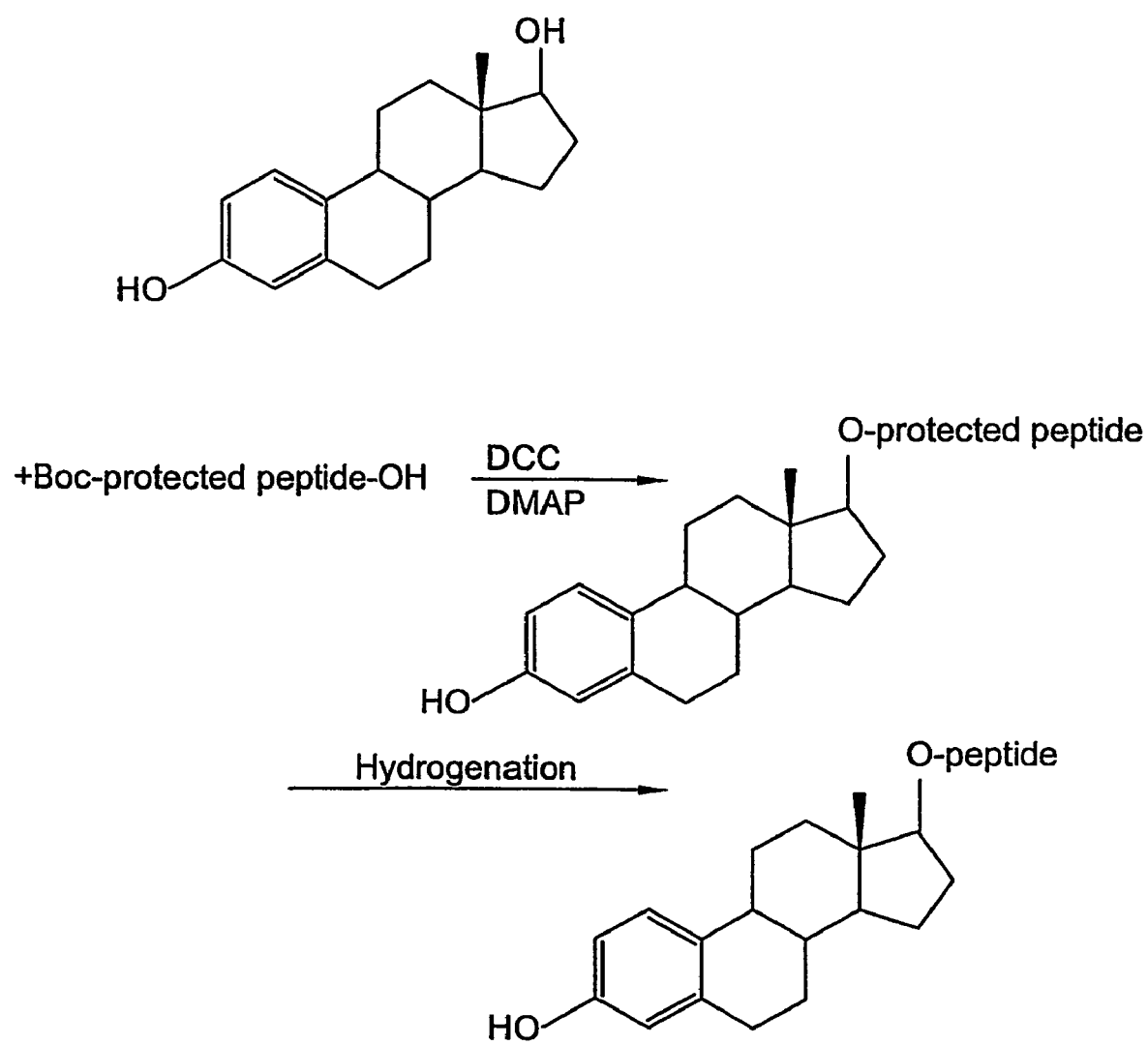
FIG. 3 contains a series of chemical reactions designed to link a peptide to a molecule of estradiol with a covalent bond.
Figure 4:
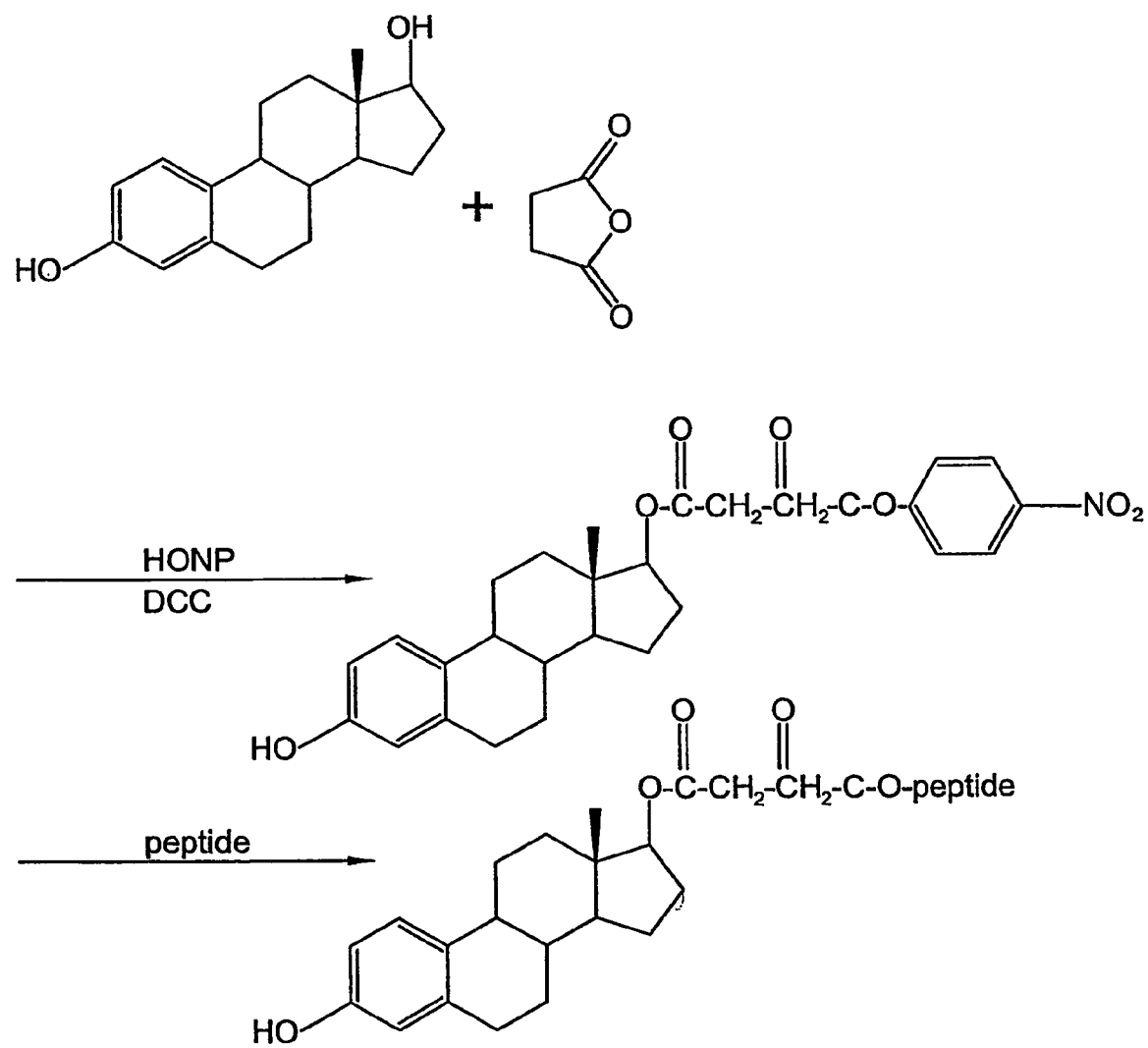
FIG. 4 contains a second series of chemical reactions for creating the same linkage as in FIG. 3.
Figure 5:
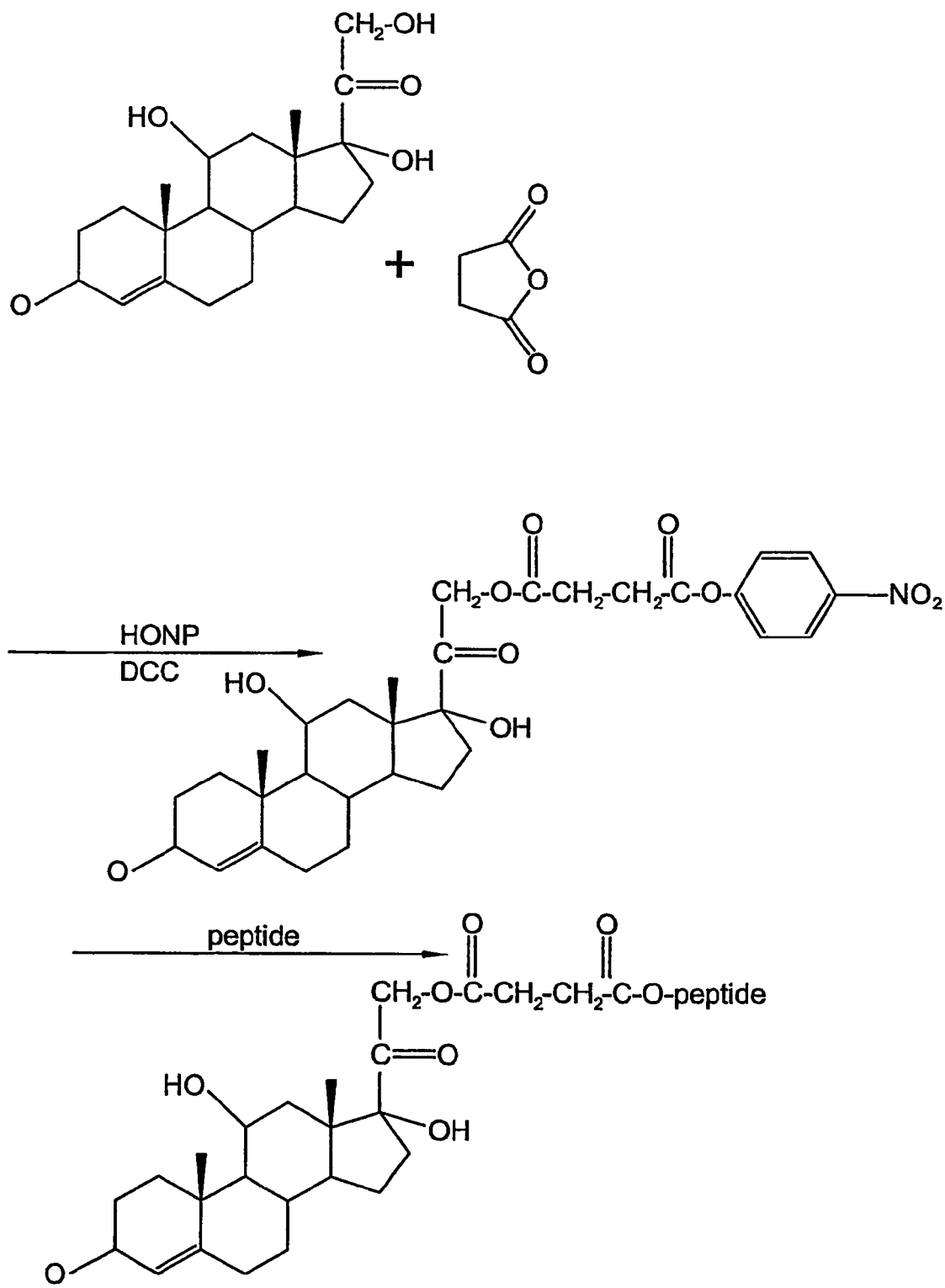
FIG. 5 demonstrates a method of linking a peptide via a covalent bond to a molecule of hydrocortisone.

Porcine spleen peptide extract has previously been reported to have therapeutic effects on human hepatitis B infections (Jurin, M., et al. Effects of low molecular weight glycoproteins in chronic hepatitis B. Hepatogastroenterology. 1996; 43(10):882-886). However, both the molecular nature of the active ingredient(s) and its pharmacology are unknown. The original extract was reported to be a mixture of glycopeptides, and the anti-HBV activity was postulated to be mediated through the stimulation of the immune system. Being a mixture of undefined molecular composition, it is not possible to optimize the therapeutic action of the individual active components in the mixture. Also, since the extract is of animal origin, the possibility of transmission of unknown animal disease to human cannot be ruled out. In order to single out the active ingredient and optimize its therapeutic action, with the ultimate aim of synthesizing the individual active ingredients chemically, the molecular composition of the extract was analyzed and the therapeutic activity of each of the components was tested. Many of the peptides in the extract were found to have anti-HBV activity, with CMS017 being the strongest HBV inhibitor in vitro, as reported below in Example 1. CMS017 was also found to have immuno-stimulating properties as reported below in Example 2. CMS017 has the sequence IVTNTT (SEQ ID NO:1) and was synthesized using L-amino acids. The finding that CMS017 has anti-viral and immuno-stimulating properties suggests that the IVTNTT (SEQ ID NO:1) molecule, larger molecules containing this molecule, including larger peptides and peptides that contain within their sequence the sequence of this peptide, and functional derivatives of IVTNTT (SEQ ID NO:1), may be useful as compound for boosting the immune system, antiviral agents, pharmaceuticals and food supplements.

It is understood that it may be possible to add additional amino acids to the amino or carboxyl termini of a peptide selected from the group consisting of IVTNTT (CMS017) (SEQ ID NO:1) and functional derivatives thereof as another method of practicing the present invention. In such embodiments, a peptide selected from the group consisting of IVTNTT (CMS017) (SEQ ID NO:1) and functional derivatives thereof maintains one or more of the therapeutic or functional properties described herein. For example, in some embodiments, one or two amino acids may be added to a disclosed peptide without affecting its biological function. In further embodiments, it may also be possible to add three or four amino acids and still maintain the function of a peptide selected from the group consisting of IVTNTT (CMS017) (SEQ ID NO:1) and functional derivatives thereof. These are all referred to as variants of the same peptide. Furthermore, derivatives of a peptide, such as conservative replacement of one amino acid for another within the same functional class, may be used to practice another aspect of the present invention. For example, peptides having non-polar or hydrophobic side chains may be possible to substitute one side group for another without reducing biological activity. As a further example, linker/spacer may be inserted into the peptide to form variants, but the variants still retain their active moiety as the original peptide used in this study. These are also considered variants of the peptides. A peptide analogue as used herein, includes peptides that have amino acid molecules that mimic the structure of the natural amino acid, e.g. an analog with a different backbone structure, or D-amino acid substitution. As a further example, although the amino acids used for synthesizing the peptides are in their L optical isomeric form, peptides with one or more of the amino acids in the sequence substituted with the D-form may have similar biological activities. The term "functional derivative" as used in the claims is meant to include fragments, variants, analogues or chemical derivatives of the peptide.

"Substantially pure peptide" refers to peptides that are at least 10% w/w in purity, more preferably 20%, even more preferably 40% and much more preferably 60% and far more preferably larger than 90% pure. In the most preferred embodiment, the purity is larger than 99%. The substantially pure peptide can be used to prepare pharmaceutical and nutritional formulations that may be complex mixtures as described below.

The use of a peptide selected from the group consisting of IVTNTT (CMS017) (SEQ ID NO:1) and functional derivatives thereof in pharmaceutical formulations may be employed as possible treatment for immunological disorders or viral disease. The formulations may have a peptide selected from the group consisting of IVTNTT (CMS017) (SEQ ID NO:1) and functional derivatives thereof mixed with other active or inactive constituents, including other peptides, e.g. two to several (e.g. 3-5) peptides may be added to the same formulation with or without other ingredients. Alternatively, a peptide selected from the group consisting of IVTNTT (CMS017) (SEQ ID NO:1) and functional derivatives thereof may be used to prepare the formulation together with peptides not listed here. They can be administered in the form of intravenous, intramuscular, intracutaneous, subcutaneous or intradermal. The mode of administration may also be intra-arterial injection that leads directly to the organ of problem. Other modes of administration are transdermal, inhalation as powder or spray, and other forms of delivery known by one in the art. The formulation may also be orally taken, and may contain carriers that can be used to prevent gastric digestion of the peptide after oral intake or any other carriers known in the art (a carrier for transdermal delivery, such as liposomes, for example).

As used herein, the term "hybrid peptide" is used to refer to peptides that contain additional peptides inserted into the original biologically active peptide having the sequence specified above or its functional derivatives, but still retain substantially similar activity. The additional peptides include leader peptides that contain, for example, an amino acid sequence that is recognized by one or more prokaryotic or eukaryotic cell as a signal for secretion of the hybrid protein into the exterior or the cell. The secretion may be a direct secretion, or indirectly through secretory vesicles.

As used herein, the terminology "consisting essentially of" refers to a peptide or polypeptide which includes the amino acid sequence of a peptide selected from the group consisting of IVTNTT (CMS017) (SEQ ID NO:1) and functional derivatives thereof along with additional amino acids at the carboxyl and/or amino terminal ends and which maintains the activity of said peptides provided herein. Thus, as a non-limiting example, where the activity of a peptide selected from the group consisting of IVTNTT (CMS017) (SEQ ID NO:1) and functional derivatives thereof is to treat and/or prevent immunological disorders or a viral infection, a peptide or polypeptide "consisting essentially of" the peptide selected from the group consisting of IVTNTT (CMS017) (SEQ ID NO:1) and functional derivatives thereof will possess the activity of treating and/or preventing infection as provided herein with respect to that peptide and will not possess any characteristics in and of itself (i.e. before modification by attachment to one or more biologically active molecules) which materially reduces the ability of the peptide or polypeptide to treat immunological disorders and/or prevent viral infection or which constitutes a material change to the basic and novel characteristics of the peptide as a treatment for and/or preventor of the above disorder or disease. Thus, in the foregoing example, a full length naturally occurring polypeptide which has a primary activity other than treating and/or preventing viral infection and which contains the amino acid sequence of a peptide selected from the group consisting of IVTNTT (CMS017) (SEQ ID NO:1) and functional derivatives thereof somewhere therein would not constitute a peptide or polypeptide "consisting essentially of" the peptide selected from the group consisting of IVTNTT (CMS017) (SEQ ID NO:1) and functional derivatives thereof whose sequence is contained in the full length naturally occurring polypeptide. Likewise, in the foregoing example, a genetically engineered peptide or polypeptide which has a primary activity other than treating immunological disorders or and/or preventing viral infection but includes the amino acid sequence of a peptide selected from the group consisting of IVTNTT (CMS017) (SEQ ID NO:1) and functional derivatives thereof somewhere therein would not constitute a peptide or polypeptide "consisting essentially of" the peptide selected from the group consisting of IVTNTT (CMS017) (SEQ ID NO:1) and functional derivatives thereof whose sequence is contained in the genetically engineered peptide or polypeptide.

Those skilled in the art can readily determine whether a peptide or polypeptide consists essentially of a peptide selected from the group consisting of IVTNTT (CMS017) (SEQ ID NO:1) and functional derivatives thereof under the foregoing definitions by measuring the activity of the peptide or polypeptide using the assays for treating immunological disorders or and/or preventing viral infection, which are provided herein with respect to the IVTNTT (CMS017) (SEQ ID NO:1) peptide.

In the preferred embodiment, the terminology "consisting essentially of" may also refer to peptides or polypeptides which have less than 5 amino acid residues in addition to a peptide selected from the group consisting of IVTNTT (CMS017) (SEQ ID NO:1) and functional derivatives thereof. In a more preferred embodiment, the same terminology refers to a peptides with 2 amino acid residues in addition to a peptide selected from the group consisting of IVTNTT (CMS017) (SEQ ID NO:1) and functional derivatives thereof. In an even more preferred embodiment, the same terminology refers to a peptide with one amino acid residue in addition to a peptide selected from the group consisting of IVTNTT (CMS017) (SEQ ID NO:1) and functional derivatives thereof.

The pharmaceutical formulation may include any of the known pharmaceutical carriers. Examples of suitable carriers include any of the standard pharmaceutically accepted carrier known to those skilled in the art. These include but are not limited to, physiological saline solution, water, emulsions including oil and water mixtures or triglyceride emulsions, and other types of agents, fillers, coated tablets and capsules. The appropriate carrier may be selected based on the mode of administration of the pharmaceutical composition.

A peptide selected from the group consisting of IVTNTT (CMS017) (SEQ ID NO:1) and functional derivatives thereof may be administered via intravenous injection, intramuscular injection, intraperitoneal injection, subcutaneous injection, and subcutaneous implantation. The peptide may also be administered in any form of oral administration like tablet, capsule, suspension, solution etc, in the usual form without modification or in slow release form, or with or without gastro-enteric protection. The peptide may further be applied in any form of topic application like ointment, cream, gel, etc., with or without transdermal facilitating device. The peptide may also be interpreted into its genetic sequence and cloned into an expression system, on its own or in combination with other peptide sequences, to generate a resulting peptide molecule to make use of the activity of the peptide as described herein.

The dose of each peptide may be 1 ng-10 g per kg body weight. A preferred dose is 10 ng-10 mg per kg, and more preferably 1 µg-1 mg per kg for an injection mode of administration. However, the effective dose can be as low as 1 ng per kg body weight, since one or more of the peptides may operate through receptors that will induce a cascade of normal physiological response. Alternatively, one or more of the peptides can just be an initiator for a whole cascade of reaction. For an oral intake, the amount may be 1 ng-10 g per day per kg body weight, more preferably 0.1 µg-1 g per day per kg body weight and even more preferably 1 µg-10 mg per day.

II. Gene Therapy and Method of Treatment

Gene therapy based on the above peptide sequences is performed by designing a nucleic acid sequence that codes for one of these peptides. The nucleic acid may be synthesized chemically and operably ligated to a promoter, and cloned into an expression vector. The expression vector is then administered into the human body as the form of gene therapy for expression in the human cell. The term "genetic vectors" as used herein includes these expression vectors. Vectors that can be used for gene therapy includes adeno-associated virus (Mizuno, M. et al. (1998). Jpn J Cancer Res 89, 76-80), LNSX vectors (Miller, A. D. et al. (1993) Methods Enzymol 217, 581-599) and lentivirus (Goldman, M. J. et al. (1997) Hum Gene Ther 8, 2261-2268).

Other vehicles for peptide delivery include expression vectors encoding the desired peptide that can be transferred into an organism which can replicate in the host organism to which it is desired to administer the peptide without significant detrimental effects on the health of the host organism. For example, the expression vectors may be transferred into an organism which is not pathogenic to the host organism to which it is desired to administer the peptide. In some embodiments the expression vector produces the desired peptide in a bacterial or fungal organism which does not have significant detrimental effects on the health of the host organism to which the peptide is to be administered. For example, the expression vector encoding the desired peptide may be an expression vector which produces the desired peptide in an organism such as lactic acid bacteria, *E. Coli*, or yeast. In one embodiment, the expression vector produces the desired peptide in a microbe normally found in the mammalian gut or a microbe tolerated by the mammalian digestive tract. Some of the microbial species in which the desired peptide can be expressed include, but are not limited to, *Lactobacillus* species, such as *L. acidophilus, L. amylovorus, L. casei, L. crispatus, L. gallinarum, L. gasseri, L. johnsonii, L paracasei, L. plantarum, L reuteri, L rhamnosus* or others; *Bifidobacterium* species, such as *B. adolescentis, B. animalus, B. bifidum, B. breve, B. infantis,* B. lactis, *B. longum* or others; *Enterococcus faecalis* or *Ent. facium; Sporolactobacillus inulinus; Bacillus subtilis* or *Bacillus cereus; Escherichia coli; Propionibacterium freudenreichii;* or *Saccharomyces cerevisiae* or *Saccharomyces boulardii.*

Nucleic acid sequences that encode any of the peptides of the present invention, chemically synthesized or produced by other means, including but not limited to the reverse transcription of mRNA to produce cDNA molecules, are incorporated into expression vectors for gene transfer into the desired organisms by methods of genetic engineering familiar to those of skill in the art. The expression vectors may be DNA vectors or RNA vectors. For example, the expression vectors may be based on plasmid or viral genetic elements. The expression vectors may be vectors which replicate extrachromosomally or vectors which integrate into the chromosome.

The expression vectors comprise a promoter operably linked to a nucleic acid encoding a peptide of the present invention. The promoter may be a regulatable promoter, such as an inducible promoter, or a constitutive promoter. In some embodiments, the promoter may be selected to provide a desired level of peptide expression. In addition, if desired, the expression vectors may comprise other sequences to promote the production, presentation and/or secretion of peptides. In some embodiments a nucleic acid encoding a peptide of the present invention is operably linked to a nucleic acid sequence which directs the secretion of the peptide. For example, the nucleic acid encoding the peptide of the present invention may be operably linked to a nucleic acid encoding a signal peptide.

In some embodiments, the expression vectors which are engineered to encode the peptides of the present invention may be expression vectors which are adapted for expressing the peptide of the present invention in a bacterial species that makes up the normal gut flora of mammals, such as *Lactobacillus species* and *Bacillus subtilis* Examples of such expression vectors can be found in U.S. Pat. No. 6,100,388, to Casas, and No. 5,728,571, to Bellini, respectively. These documents are hereby expressly incorporated by reference in their entireties. It will be appreciated that any expression vector which facilitates the expression of a peptide of the present invention in an organism which is not detrimental to the health of the host organism to which the peptide is to be administered may be used.

In some embodiments, the expression vectors which are engineered to encode the peptides of the present invention may be expression vectors which are adapted for expressing the peptide of the present invention in a yeast species that is well tolerated by the mammalian gut, such as *Saccharomyces cerevisiae*; or, preferably, *Saccharomyces boulardii*, which can colonize the human gut and is used to treat certain forms of diarrhea. Yeast expression vectors can be used that constitutively express heterologous proteins and peptides, are highly stable, thus are well transmitted to progeny cells during mitosis and meiosis and may comprise coding sequence for a signal peptide or peptides that direct high levels of recombinant protein secretion. An example of such a yeast vector is given in U.S. Pat. No. 6,391,585, to Jang et al., which is hereby expressly incorporated by reference in its entirety.

The expression vectors encoding the peptides of the present invention may be introduced into the organism in which it is intended to express the peptides through techniques known in the art. These techniques include traditional methods of transforming bacteria, yeast, or other microbes, through the use of chemically competent bacterial cells, electroporation or lithium acetate transformation (for yeast), for example, as well as recent advances in the transformation of bacterial species recalcitrant to these procedures. In some embodiments, the expression vectors are introduced into lactic acid bacteria known to be recalcitrant to transformation using the method disclosed by Leer et al. (WO 95/35389), the disclosure of which is incorporated herein by reference in its entirety. The introduced sequences may be incorporated into microbial chromosomal DNA or may remain as extrachromosomal DNA elements.

This genetically engineered microbe containing the expression vector can then be inoculated into the alimentary canal, vagina, trachea etc. to achieve sustained immunotherapy. In some embodiments, the organisms expressing the peptides of the present invention are ingested in an inactive form or, preferably, in live form. In the gut these microorganisms produce said peptides, release them into the lumen by secretion or by lysis of the microorganism or otherwise present the peptides to the host, whereby the peptides produce their intended effect upon the host organism. In other embodiments, peptides are presented to the host at the mucous membrane of the nasal passages, vagina or the small intestine.

Another method of the treatment is the use of liposomes as a means for delivering the specific nucleic acid to the cells in the human body. The nucleic acid (such as an expression vector containing a nucleic sequence that encodes a peptide selected from the group consisting of IVTNTT (CMS017) (SEQ ID NO:1) and functional derivatives thereof) is delivered in an environment that encourages cellular uptake and chromosomal incorporation as described in Gao, X. and Huang, L. (1995) Gene Ther 2, 710-722 and U.S. Pat. No. 6,207,456. Alternatively, the peptide itself can be encapsulated in the liposome and delivered directly, using a method described in U.S. Pat. No. 6,245,427. All the scientific publications and patents indicated above are incorporated herein by reference in their entireties.

The nucleic acid sequences useful for the above-mentioned gene therapy and method of treatment include sequences that code for these peptides and functional derivatives thereof. Any one of the numerous nucleic acid sequences may be used to code for these peptides and their derivatives based on the degenerate codon system.

The following references are incorporated herein by reference in their entireties.
1. Principles of Pre-clinical Research of New Drugs, People's Republic of China. 1993, 7:134-135 Shuyun Xu, Rulian Bian, Xiu Chen. Methodology of pharmacological experiment. People's Health Publishing House. 1991, 1221-1234
2. Principle of new drug research in pre-clinic issued by Ministry of Health, People's Republic of China. 1993, 7:140
3. Jinsheng He, Ruizhu Li, Tingyi Zong. The study on MTT reduction method of testing NK cell activity. China Immunology Journal. 1996, 1(6): 356-358
4. Qian Wang. Modern medical experiment method. People's Health Publishing House. 1998, 482-483
5. Principle of new drug research in pre-clinic issued by Ministry of Health, People's Republic of China. 1993, 7: 141
6. Principle of new drug research in pre-clinic issued by Ministry of Health, People's Republic of China. 1993, 7: 132-133
7. Principle of new drug research in pre-clinic issued by Ministry of Health, People's Republic of China. 1993, 7: 128-129
8. Yuanpei Zhang, Huaide Su. Phamalogical experiment (second edition). People's Health Publishing House. 1998, 137-138
9. Jiatai Li, clinical pharmacology (second edition). People's Health Publishing House. 1998, 1338-1339.

III. Peptide Conjugations to and Formulations with IVTNTT (CMS017) (SEQ ID NO:1) and Derivatives Thereof The biologically active peptides of the present invention may be conjugated to other biologically effective or useful molecules to provide an additional effect or use or to enhance their therapeutic effectiveness. Many potential conjugating molecules, their biological effects and the methods for conjugation of the molecules to peptides are known in the art. For other candidate conjugation partners, chemical reactions for conjugating the instant peptides thereto can be deduced by one skilled in the art without undue experimentation. Effective molecules are described below. Specific examples of how various peptides according to the present invention may be conjugated to their effective molecules and the biological properties of the resulting conjugation product are described. It is understood that other peptides of the instant invention may also be conjugated in similar reactions.

The peptide IVTNTT (CMS017) (SEQ ID NO:1) and functional derivatives thereof can have distinct therapeutic effects on particular cells or tissue types. One important objective of conjugating molecules to peptide drugs is the targeting of the peptide to a particular location or compartment within the body of an individual being treated. In this way, the peptide drug and its effects can be concentrated at the location of the cell or tissue type on which it has the intended therapeutic effect. This can augment the effect that a similar molar amount of the free, unconjugated peptide would have. Conversely, the dosage of a conjugated peptide drug that is targeted to its therapeutic active site can be significantly lower than the dosage required to get the same therapeutic effect from the free, unconjugated form of the drug.

Another beneficial effect of targeting a peptide drug to the site where its activity is most desired is the reduction of unwanted side effects. A peptide drug that is administered in order to effect a change in a particular cell or tissue type can also act in other locations within an individual, sometimes with detrimental results. By targeting the peptide to the desired location of activity via conjugation to a targeting molecule, the concentration of peptide elsewhere in the individual and the subsequent side effects can be reduced.

Peptides comprising, consisting essentially of, or consisting of a peptide selected from the group consisting of IVTNTT (CMS017) (SEQ ID NO:1) and functional derivatives thereof can be conjugated to a variety of molecules for targeting to different locations throughout the body of an individual. Any of the conjugation technologies described below for targeting a peptide to a desired location, as well as other conjugation technologies familiar to those skilled in the art, may be employed with any of the peptides of the present invention. For example, the selective delivery of an anti-hepatitis B drug to liver cells has been demonstrated (Fiume et al., Ital J Gastroenterol Hepatol, 29(3):275, 1997, which is incorporated herein by reference in its entirety). In this study, researchers conjugated adenine arabinoside monophosphate (ara-AMP), a phosphorylated nucleoside analogue active against hepatitis B virus, to lactosaminated human albumin, a galactosyl-terminating macromolecule. Hepatocytes express a receptor protein that interacts with terminal galactosyl residues with high affinity. Through binding to this receptor, the conjugated drug will be selectively taken up by hepatocytes. After absorption, the conjugated drug is delivered to lysosomes, where the bond between the two components of the conjugated drug is cleaved, releasing ara-AMP in its active form. In the study cited above, the conjugated drug was as effective as free ara-AMP in treating patients with chronic hepatitis B infections, but did not cause the clinical side effects, such as neurotoxicity, that the administration of free ara-AMP causes. Such an approach can be used with any of the peptides of the present invention.

In a related study to the one above, by the same research team (Di Stefano et al., Biochem. Pharmacol., 61(4):459, 2001), an anti-cancer chemotherapeutic agent, 5-fluoro 2-deoxyuridine (FUdR), was conjugated to lactosaminated poly-L-lysine in order to target the compound to the liver and treat liver micrometastases. The drug is selectively taken up by liver cells, which cleave the bond between FUdR and the targeting molecule. A portion of the free FUdR will then exit the liver cells and a localized therapeutic concentration of the anti-cancer agent is created. This concentration is sufficient for pharmacological activity on the metastatic cells that have infiltrated the liver. Because the drug is selectively concentrated in the liver, the dosage of the conjugated drug can be significantly less than the smallest pharmacologically active dosage of the free, unconjugated compound. This strategy can be utilized with any of the peptides of the present invention. For instance, conjugation of lactosaminated poly-L-lysine to a peptide selected from the group consisting of IVTNTT (CMS017) (SEQ ID NO:1) and functional derivatives thereof could significantly reduce the dosage necessary to treat a viral infection involving liver tissues.

The targeting of compounds to particular tissues or cell types within the body has been achieved for a number of different tissues or cell types. For example, tumor cells often express abnormally high levels of peptide hormone receptors on their surfaces, such as bombesin, lutenizing hormone-releasing hormone, and somatostatin. In one study, the anticancer compound paclitaxel (taxol) has been selectively targeted to hormone-secreting tumor cells that express somatostatin receptors at a high density by conjugating the drug with octreotide, an analog of somatostatin. The ostreotide-conjugated taxol was just as effective as free taxol but with reduced toxicity to normal cells (Huang et al., Chem. Biol., 7(7):453, 2000). Using the techniques of Huang et al. to conjugate peptides of the present invention to analogs of peptide hormone receptor agonists would create a treatment specifically targeting cells expressing high levels of that particular peptide hormone receptor. This approach can be adapted to target cells overexpressing any number of peptide hormone receptors. In another example of targeting a drug to a specific tissue type, poly (L-aspartic acid) was used as a carrier molecule to target drug delivery to colon cells specifically (Leopold et al., J. Pharmacokinet. Biopharm., 23(4): 397, 1995).

Beyond the specific targeting of a peptide drug to a particular cell or tissue type, conjugation of peptides comprising, consisting essentially of, or consisting a peptide selected from the group consisting of IVTNTT (CMS017) (SEQ ID NO:1) and functional derivatives thereof to carrier molecules can provide other ways to enhance the delivery of peptide drugs, thereby augmenting or otherwise improving their therapeutic effects. Any of the conjugation technologies described below may be used with any of the peptides of the present invention, as with other technologies familiar to those skilled in the art. The effectiveness of any drug will be hampered if the compound cannot be delivered to its target efficiently. A drug must be transported, actively or otherwise, to the site of its activity without substantial loss of activity due to metabolic processing or degradation. Peptide drugs are subject to the activity of peptidases and, as highly charged molecules, can be refractory to transport across lipid cell membranes and endothelial cell membranes, such as the blood-brain barrier. Conjugation to other molecules provides a way to protect peptides from degradation and to enhance the absorption of peptide drugs into cells or anatomical compartments that would normally exclude the compounds.

By allowing peptides access to locations within the body from which they would normally be excluded, conjugation techniques can open up new routes for administration of the drug. In Patel et al., Bioconjugate Chem., 8(3):434, 1997, the chemistry of which is detailed in Example 5 below and which is incorporated herein by reference in its entirety, researchers conjugated a peptide drug known to be a potent analgesic, the heptapeptide deltorphin, to an organic molecule that was specifically designed to allow the peptide to cross the blood-brain barrier. This allows the drug to be administered intravenously instead of by intracerebro ventricular injection.

The carrier molecule in Patel et al. was designed to specifically target those endothelial cells that comprise the blood-brain barrier in addition to allowing the peptide to get across the barrier. Endothelial cell membranes throughout the body, including the blood brain barrier, are heterogeneous with regards to the sequence specificity and concentration of membrane-bound endopeptidases that are displayed on their surfaces. The design of the molecule exploits this characteristic to enable targeting of the carrier molecule and its cargo. The molecule contains three fatty acid chains whose free ends are capped with the dipeptide Arg-Pro, which will interact preferentially with the endopeptidases of the blood brain barrier. The transport of the charged peptide drug molecule is then enabled by the lipophilic fatty acids chains. Thus the dipeptide-capped triglyceride molecule permits both the targeting and the transport across the blood brain barrier.

Conjugation methods can also enhance the kinetics of a peptide drug's activity. Any of the conjugation technologies described below for enhancing the kinetics of a peptide's activity as well as other conjugation technologies familiar to those skilled in the art may be employed with a peptide comprising, consisting essentially of or consisting of a peptide selected from the group consisting of IVTNTT (CMS017) (SEQ ID NO:1) and functional derivatives thereof. Patel et al. found that the conjugated form of the analgesic peptide was not only able to enter the brain from the bloodstream, but had sustained action in comparison to the free peptide as well. The intravenously administered drug took longer to have a therapeutic effect, but the effect lasted longer and decreased more slowly than the effect of the free peptide injected intracranially. The researchers found that the conjugated peptide molecule is remarkably stable in serum, yet had no effect when injected intracerebro ventricularly, indicating that the carrier molecule is likely degraded and removed during its transport from the bloodstream to the brain. They suspect that the time required to transport the conjugate and degrade the carrier molecule is the cause of the altered kinetics. Regardless of the mechanics of the delay, in a clinical setting, the intravenous stability of the conjugated peptide molecule and the prolonged onset and activity of the drug's effects would mean that it could be administered less frequently. A less frequent and thus more convenient dosing schedule enhances the practical value of the drug as a treatment option.

As would be apparent to a person of skill in the art, the techniques and procedures of Patel et al. are readily adaptable to the delivery of any peptides that fall within a limited size range, including any of the peptides of the present invention. For example, a peptide of the present invention that treats and/or prevents immunological disorders or viral infection, such as IVTNTT (CMS017) (SEQ ID NO:1), could be conjugated to the same molecule used by Patel et al. In the treatment of an individual with an infection that affects the brain, the conjugated molecule would allow IVTNTT (CMS017) (SEQ ID NO:1) access to the brain from the bloodstream and allow IVTNTT (CMS017) (SEQ ID NO:1) to exert its effects on cells or tissues in the brain. Modifications to alter the targeting of the carrier molecule would also be apparent to such a person. The targeting feature of the carrier molecule is a function of the identity of the two amino acids that comprise the dipeptide mask at the end of the fatty acid chains. The Arg-Pro dipeptide interacts preferentially with the set of membrane-bound endopeptidases found on the surface of the blood brain barrier's endothelial membrane. Other endothelial cells and membranes could potentially be targeted by other dipeptide combinations.

Conjugation has also been used by researchers to create peptide drugs that can be effectively absorbed through the digestive tract or transdermally. Any of the conjugation technologies for enhancing absorption described below, as well as other conjugation technologies familiar to those skilled in the art, may be used to enhance the absorption of a peptide comprising, consisting essentially of or consisting of a peptide selected from the group consisting of IVTNTT (CMS017) (SEQ ID NO:1) and functional derivatives thereof. Kramer et al. describe a procedure for the coupling of peptide drugs to bile acids. The absorption rate for the conjugated molecule following oral delivery of the compound is significantly enhanced as compared to the peptide alone (J. Biol. Chem., 269(14): 10621, 1994). Toth et al. (J. Med.

Chem., 42(19):4010, 1999) describe the conjugation of a peptide drug with anti-tumor properties to lipoamino acids (LAA) or liposaccharides (LS), in order to increase the absorption rate and enhance the delivery of the anti-cancer peptide to its active site. In their study, a derivative of somatostatin that shows strong anti-proliferative properties, but has impaired pharmokinetics, is conjugated to either LAA or LS. The resulting conjugate drug has improved absorption profiles across skin and gut epithelium and increased resistance to degradation while still active against tumor cells. These techniques would be very useful in conjunction with any of the peptides of the present invention. By increasing the rate of absorption of the molecule across the intestinal epithelium, more of the peptide can be delivered to the bloodstream and exert its effect on the individual being treated.

Conjugation may also be used to provide sustained release of a peptide drug. Any of the conjugation technologies for providing sustained release, as well as other conjugation technologies familiar to those skilled in the art, may be used to provide sustained release of a peptide comprising, consisting essentially of or consisting of a peptide selected from the group consisting of IVTNTT (CMS017) (SEQ ID NO:1) and functional derivatives thereof. As seen above in the work of Patel et al., the sustained delivery of a peptide drug can be achieved with conjugation methods. Another example is the work of Kim et al. (Biomaterials, 23:2311, 2002), where recombinant human epidermal growth factor (rhEGF) was conjugated to polyethylene glycol (PEG) before microencapsulation in biodegradable poly(lactic-co-glycolic acid) (PLGA) microspheres. Microencapsulation in PLGA has been used by several groups to deliver various growth factors and morphogenic proteins (Meinel et al., J. Controlled Rel., 70:193, 2001). Through conjugation to PEG, rhEGF became resistant to forming water-insoluble aggregates and to adsorption to the water-organic phase interface during micelle formation with PLGA as compared to unconjugated, free rhEGF. The pharmokinetics of the formulation with the conjugated hormone were improved, showing longer lasting, steadier and overall greater drug activity than with the free hormone, which the researchers speculate is due to the enhanced physical stability of the hormone conjugated to PEG. A similar strategy could be employed to create sustained release formulations of any of the peptides of the present invention. For example, as seen in Example 1 below, IVTNTT (CMS017) (SEQ ID NO:1) exhibits potent antiviral effects. By conjugating PEG to this peptide and incorporating the conjugated drug into PLGA microspheres, the antiviral effects of IVTNTT (CMS017) (SEQ ID NO:1) can be longer lasting and more stable, as the dosing of the drug, as it is being released from its PEG conjugate, is more even and ensures a more constant delivery of the peptide drug to the site of infection.

Prolonged release of a peptide drug can significantly enhance its activity. Any of the conjugation technologies for providing prolonged release of a peptide described below, as well as other conjugation technologies familiar to those skilled in the art, may be used to provide prolonged release of a peptide comprising, consisting essentially of or consisting of a peptide selected from the group consisting of IVTNTT (CMS017) (SEQ ID NO:1) and functional derivatives thereof. Oldham et al. (Int. J. Oncology, 16:125, 2000) compares the anticancer agent paclitaxel against a new form of the drug, paxlitaxel conjugated to poly(L-glutamic acid) (PG-TXL). PG-TXL appeared to have superior anti-tumor activity compared to free paclitaxel, suggesting that the drug has superior pharmokinetic properties or maybe even a superior method of action. However, investigators found that PG-TXL exerted its effects by the same mechanism of action as the free drug, inducing cell cycle arrest by disturbing the polymerization of microtubules subunits. Evidence suggests that the superior anti-tumor activity of the conjugated drug arises from a continuous and steady release of the free drug from the conjugate, maintaining its therapeutic concentration for a longer period as compared to administration of the free peptide. The addition of poly(L-glutamic acid) tail to a peptide of the invention with infection-fighting properties could enhance those properties as well.

The enzymatic degradation of peptides may, in some cases, reduce the effectiveness of the peptides as drugs. Any of the conjugation technologies for reducing enzymatic degradation of a peptide described below, as well as other conjugation technologies familiar to those skilled in the art, may be used to reduce the enzymatic degradation of a peptide comprising, consisting essentially of or consisting of a peptide selected from the group consisting of IVTNTT (CMS017) (SEQ ID NO:1) and functional derivatives thereof. Researchers have developed numerous approaches to protect peptides from luminally secreted proteases in the gut as well as membrane-bound peptidases. The latter are found on the surface of all mucosal tissues, the crossing of which is often the route of entry for peptide drugs. Bernkop-Schurch et al. (J. Drug Target., 7:55, 1999) report the creation of peptide drug formulations containing inhibitors of pepsin. An analogue of pepstatin was covalently attached to mucoadhesive polymers; this novel pepsin inhibitor was included in tablets containing insulin. After incubation under laboratory conditions simulating digestion, all of the insulin from control tablets was metabolised, whereas nearly 50% of the insulin from tablets containing the inhibitor was protected from degradation. In another study, the same group utilized protease inhibitors at dosages that would normally cause toxic side effects to inhibit degradation of biologically active peptides (Bernkop-Schnurch et al., Adv. Drug Del. Rev., 52:127, 2001). This approach utilizes chitosan, an aminopolysaccharide related to cellulose that is extracted from chitin, a major structural polysaccharide found in crustaceans and other organisms. By conjugating the protease inhibitors to chitosan and including this conjugated molecule in the formulation of the peptide drug, significant inhibition of digestive tract proteases was seen, increasing the bioavailability of the peptide, without the side effects that would be expected with administration of free protease inhibitors. In the study, a variety of protease inhibitors alone and in combination were utilized for conjugation to the chitosan carrier. A chitosan-EDTA conjugate inhibited endogenous proteases as well, by binding mineral co-factors required by certain proteases for activity. As would be readily apparent to one with skill in the art, a large number of possible combinations between carrier molecules and effector moieties could be created to provide beneficial properties to peptide formulations, any of which could easily be adapted for use with a peptide of the present invention. By creating a formulation for oral delivery of the peptide using protease inhibitors bound to chitosan, oral delivery of a peptide of the invention could be used in place of intramuscular injections. This approach does not rule out using the more absorbable, conjugated version of a peptide selected from the group consisting of IVTNTT (CMS017) (SEQ ID NO:1) and functional derivatives thereof (discussed in a paragraph above) in this formulation, to create an even greater level of bioavailability for this peptide and its derivatives.

In addition to being targeted to a location by another molecule, peptides themselves can serve as the molecule that targets. Any of the conjugation technologies for using a peptide to target a molecule to a desired location described below, as well as other conjugation technologies familiar to those skilled in the art, may be used with a peptide comprising, consisting essentially of or consisting of a peptide selected from the group consisting of IVTNTT (CMS017) (SEQ ID NO:1) and functional derivatives thereof. For example, researchers have taken the anticancer drug difluoromethylornithine (DFMO) and conjugated it to a peptide for targeting purposes. DFMO is a highly cytotoxic agent that is effective in killing a variety of tumor cell types. However, since it is rapidly cleared from the body, its therapeutic value is limited. In this study, DFMO has been conjugated to a particular fragment of α melanotropin and an analogue of the fragment containing two amino acid substitutions that was shown to bind preferentially to the melanotropin receptors on a human melanoma cell line (Suli-Vargha et al., J. Pharm. Sci., 86:997, 1997). To facilitate the liberation of DFMO from the peptide fragments by aminopeptidases, the drug was conjugated to the N-terminal ends of the peptides. The researchers found that the conjugated drugs are more effective at killing melanoma cells that the unconjugated drug alone.

The effects of the peptides of the present invention may be due in part to a targeting ability inherent in the peptides themselves. For instance, like the α melanotropin fragment, a particular peptide of the invention may bind to a certain receptor found on the surface of a distinct type of cell. By using that peptide as a conjugant, a drug could be targeted to the location of those cells within the body of an individual being treated with the drug.

Peptides as conjugates can serve functions other than targeting. Any of the conjugation technologies for enhancing the therapeutic effectiveness of a peptide described below, as well as other conjugation technologies familiar to those skilled in the art, may be used to enhance the therapeutic effectiveness of a peptide comprising, consisting essentially of or consisting of a peptide selected from the group consisting of IVTNTT (CMS017) (SEQ ID NO:1) and functional derivatives thereof. Fitzpatrick et al. have improved upon a conjugated anticancer agent by using a peptide spacer between the two molecules (Anticancer Drug Design, 10:1, 1995). Methotrexate had already been conjugated to human serum albumen (HSA) to increase its uptake by and activity against tumor cells. Once taken up by a cell, some of the methotrexate is liberated from the conjugate by enzymes in the lysosome and can then exert its cytotoxic effects. By inserting a four amino acid linker peptide between the methotrexate and the HSA that is easily digested by lysosomal enzymes, the amount of active methotrexate generated within cells from the conjugate molecule was increased. The peptides of the present invention may be exerting their effects through specific interaction with particular enzymes. By incorporating a peptide of the invention into a conjugated molecule as a linker segment between a drug and its carrier molecule, or in addition to another linker segment, the pharmacokinetics can be altered. This can create a pro-drug that is more resistant or more susceptible to the activity of proteases, which subsequently decreases or increases the rate of drug molecule release from the conjugate. As seen in the examples of conjugated chemotherapy agents above, altering that rate of drug molecule delivery can greatly enhance the effectiveness of a drug.

The effects of a drug on a particular cell may be altered depending upon other factors such as the activation state of a cell or the presence of other molecular signals near or within the cell. In some cases, in order for a drug to have an effect, another molecule or signal needs to be present. Damjancic et al. (Exp. Clin. Endocrin., 95:315, 1990) studied the effects of human atrial natriuretic peptide (hANP) on patients with deficient endogenous glucocorticoid synthesis. The peptide was given to patients during a withdrawal of glucocorticoid therapy or during subsequent resumption of therapy using dexamethasone. Patients responded to hANP with an increase in diuresis and sodium excretion only when the peptide hormone was given during concomitant dexamethasone treatment. Treatment with hANP during withdrawal of glucocorticoid therapy had no effect. The effect of concurrent steroid hormone administration can also be to enhance the activity of a peptide. In a report from Zhu et al. (Acta Pharm. Sinica, 28:166, 1993), the activity of the analgesic peptide kyotorphin (KTP) was significantly enhanced by conjugation to hydrocortisone via a short linker segment, as compared to the action of the peptide alone. No effect was seen with the administration of hydrocortisone alone.

The results of these studies illustrate the ability of steroid hormones as conjugated molecules or as ingredients in formulations can allow or enhance the activity of biologically active peptides. Any of the peptides of the present invention may also be modulated or activated by conjugation to or co-application of steroid hormones. The techniques of Zhu et al. can be readily adapted for conjugation of steroid molecules to peptide of the present invention. FIGS. 1 through 5 also provide exemplary step-wise synthesis reactions for linking steroid hormones to any of the peptides of the present invention.

The examples presented above provide exemplary ways to augment the usefulness and the activities of any of the peptides of the invention. Further developments in this field will help overcome the barriers to creating effective peptide-based clinical treatments. As would be apparent to one with skill in the art, the techniques, reagents and protocols developed for use in peptide biochemistry, pharmaceutical research and clinical testing are all readily appliable to any of the peptides of the present invention.

EXAMPLES

Example 1

In Vitro Study of CMS017

CMS017 has the sequence IVTNTT (SEQ ID NO:1) and was synthesized using L-amino acids. The effect of CMS017 treatment on cells transfected with hepatitis B virus was examined in this experiment.

1. MATERIALS

CMS017 was custom synthesized (using L-amino acids) by American Peptide Company, Inc., U.S.A., and diluted to the desired concentration with normal saline.

The hepG 2 2.2.15 cell line, transfected by hepatitis B virus (HBV), was supplied by the National Center for Drug Screening (Shanghai, China) and the Department of Infectious Diseases of the First Hospital affiliated to Beijing University.

Cell culture media (MEM) was manufactured by GIBCO Company.

ELISA kits for HBsAg and HBeAg were purchased from Shanghai Shiye Kehua Biotech. Company.

Fluorescent quantitative PCR kits for the determination of HBV-DNA were purchased from Da-An gene company of Zhongshan Medical University.

2. METHODS a. Inhibitory effect of CMS017 on HBsAg and HBeAg at maximum non-toxic concentration in vitro 2.2.15 cells, growing at logarithmic phase, were harvested and re-suspended in MEM culture medium (containing 10% calf serum, 100 mg/ml penicillin, and 100 U/ml streptomycin) as a $2\times10^6$/ml cell suspension. The suspension was inoculated into a 24-well cell culture plate with 1.5 ml per well, and incubated at 37° C., 5% $CO_2$ for 48 hours. The test substance CMS017 was diluted and added to the 2.2.15 cultures to final concentrations of 0, 50, 100, 200, 400, 800 µg/ml, with 3 parallel samples per concentration. The cells were then incubated at 37° C., 5% $CO_2$. The supernatant was refreshed on days 3 and 6. The cytotoxicity of CMS017 on 2.2.15 cell cultures was then observed with MTT staining on day 8, and the maximum non-toxic concentration of CMS017 was determined.

The preparation and incubation of cell suspensions were repeated as above with the determined maximum non-toxic concentration of CMS017, and with parallel negative and positive controls (lamivudine with the same concentration as CMS017 was used as the positive control). On the $8^{th}$ day, the titers of HBsAg and HBeAg in the cell culture supernatants were determined by ELISA[1,2], using conditions described by the kit supplier. The inhibition percentage of each test substance was calculated as shown below.

Inhibitory percentage (%)=(blank control−sample)/
blank control×100

Cell survival percentage (%)=sample $(A_{595}-A_{650})$/
blank control $(A_{595}-A_{650})$×100 b. Inhibitory Effect of CMS017 on HBV-DNA In Vitro

Cell suspensions were prepared and incubated as described in Method 1 above. In this experiment, vidarabine monophosphate (Ara-AMP) was used as the positive control substance. The test substances, CMS017 or Ara-AMP, were diluted and added to the activated cell cultures to final concentrations of 0, 20, 40, 80, 160, 320 µg/ml, with 3 parallel samples per concentration. The culture media, with added test substance, were exchanged on days 3 and 6. On the $8^{th}$ day, the supernatants of the cell cultures were harvested for the determination of HBV-DNA concentrations by fluorescent quantitative PCR[3,4], using the method described by the kit supplier. The cultured cells were taken for analysis of the cytotoxicity of each test substance. The inhibitory percentage of the drug was calculated in the following manner:

Inhibitory percentage (%)=(blank control−sample)/
blank control×100

Cell survival percentage (%)=sample $(A_{595}-A_{650})$/
blank control $(A_{595}-A_{650})$×100

$TC_{50}$ was defined as the test substance concentration at which the percentage of surviving cells in the test group is 50% of that of the control group. $IC_{50}$ was the test substance concentration at which the percentage of reduction of HBV-DNA concentration is 50% compared to control. These were determined by plotting the corresponding percentage against the test substance concentrations. The selection index (SI) was calculated as $TC_{50}/IC_{50}$. The bigger the value of SI, the higher the inhibition activity of test substance is and the less cytotoxic it is.

Statistical significance was analyzed by the t-test, using the software SPSS.

3. RESULTS a. The Inhibitory Effect of CMS017 on HBsAg and HBeAg

The maximum non-toxic concentration of CMS017 was found to be 400 µg/ml. Table 1 showed the calculated inhibitory percentage at this maximum non-toxic concentration.

TABLE 1

Inhibitory effect of CMS017 on HBsAg and HBeAg at 400 µg/ml

| Test substance | Inhibition ratio of HBsAg | Inhibition ratio of HBeAg |
| --- | --- | --- |
| CMS017 | 68.6%* | 62.2%* |
| Lamivudine | 29.6%* | 35.4%* |

*$p < 0.01$ comparing with negative control b. The Inhibitory Effect of CMS017 on HBV-DNA

Table 2 showed the $TC_{50}$, $IC_{50}$, and SI of the test substances, and Table 3 showed the inhibitory percentage of the same.

TABLE 2

Inhibitory effect of drugs on HBV-DNA

| Drug | $TC_{50}$(µg/ml) | $IC_{50}$(µg/ml) | SI |
| --- | --- | --- | --- |
| CMS017 | 1332.5 | 2.3 | 577.7 |
| Ara-AMP | 64.2 | 11.4 | 5.6 |

TABLE 3

Drugs' inhibitory ratio for supernatant HBV-DNA, at the concentration of 160 µg/ml

|  | CMS017 | Ara-AMP |
| --- | --- | --- |
| inhibitory percentage | 90.8%* | 89.1%* |

*$p < 0.01$ comparing with negative control

4. CONCLUSION

It has been reported that porcine spleen glycopeptides have therapeutic effects on human hepatitis B infection. However, the molecular nature of the active ingredient(s) remained unclear. In order to identify the concerned active ingredient, with the ultimate aim of chemically synthesizing it, optimizing its therapeutic administration, and eliminating unwanted side effects caused by other co-existing contaminating components, the porcine spleen extract was analyzed at a molecular level (using the Keck facility of Yale University). Individual peptide components were then synthesized chemically and each of these peptides was screened for anti-viral activity. A large number of the peptides were observed to have various levels of antiviral activity in vitro. Among these, CMS017 is one of the peptides with the strongest anti-viral activity in vitro.

In this study, CMS017 was able to inhibit the level of HBV-DNA in vitro, with statistical significance. The 50% inhibition concentration ($IC_{50}$) was 2.3 µg/ml, and the HBV-DNA inhibitory percentage was 90.8% at a concentration of 160 µg/ml. It is concluded that CMS017 is an anti-viral agent in vitro, and is a candidate for development into an antiviral therapeutic pharmaceutical for the treatment of viral infections such as hepatitis B.

5. REFERENCES

1. Wu Qing, et al. The inhibition of hepatitis B viral gene expression by antisense oligo deoxynucleotides. Journal of Anhui University of Medical Science. 2001; 36(6): 434-437
2. Gao Yong, et al. A study of hepatitis B virus (HBV) anti-genome and its inhibitory effect on HBV replication. Zhong Hua Nei Ke Za Zhi. 2001; 40(4): 243-246.
3. Ausubel F. M, et al. Short Protocols in Molecular Biology. Science Publishing House. Beijing, 1998, the first edition (translation). P 596-598
4. Tian Hua, et al. Determination of the serum HBV-DNA of the patients with hepatitis B by FQ-PCR. Journal of Shanghai Medical Laboratory. 2001; 16(6): 363-364

Example 2

In Vivo Study of CMS017

The following animal study was performed to investigate the effect of CMS017 on the T lymphocyte transformation of mice induced by ConA.

1. MATERIALS a. Experimental Animals

BALB/c mice, 18-22 g, male, provided by VITAL RIVER, Inc., Beijing, PR China.

b. Reagents

CMS017: custom synthesized by CS Bio, U.S.A.
Fetal bovine serum, and RPMI-1640 cell culture medium: Gibco, U.S.A.
MTT and ConA: Sigma, U.S.A.
rhIL-2: Shanghai Huaxin Biotech Inc., China

2. METHOD a. Grouping and Administration

The BALB/c mice were randomly divided into CMS017 dose I group (200 µg/kg/day), CMS017 dose II group (50 µg/kg/day), recombinant human IL (rhIL)-2 group ($3\times10^5$ IU/kg/day), and saline groups (0.5 ml/day). Twelve mice per group.

Test substances were all dissolved in saline and injected intraperitoneally at (i.p.) 0.5 ml/day for 28 continuous days, once per day.

b. The Effect of Peptides on Cellular Immunity i. Preparation of Spleen Cell Suspension [1,2]

The day after the last test substance administration, the mice were sacrificed by cervical dislocation. The spleen was isolated aseptically and manually dispersed in cold D-Hank's solution using an injection needle. The dispersed cell suspension was further sieved through a 100 gauge 150 µm diameter stainless steel sieve. After centrifugation at 200 g for 10 minutes, the supernatant was discarded. The cell pellet was resuspended in 10 volumes of Tris-$NH_4Cl$ buffer and then incubated for 10 minutes at room temperature. The suspended cells were collected by centrifugation at 150 g for 10 minutes. The cells were washed 2-4 times with cold D-Hank's solution by resuspending and collecting by centrifugation as described above. The washed cells were then diluted to the desired cell densities in RPMI-1640 culture medium, containing 10% fetal bovine serum.

ii. The Effect of Peptides on T Lymphocyte Transformation [1,2]

Spleen cells of density $4\times10^6$/ml were placed onto a 96 well cell culture plate, 100 µl/well, three parallel wells of both the assay sample and the control sample per mouse. To each assay well, 100 µl/well of ConA at 5% g/ml in RPMI-1640 was added, and 100 µl/well of plain RPMI-1640 was added to the control wells. The cells were incubated for 68 hrs at 37° C., 5% $CO_2$. The cells were then pelleted by centrifugation at 150 g for 10 minutes. 100 µl/well of MTT at 0.5 mg/ml in RPMI-1640 was added to the cell pellets and the cells were resuspended by shaking for 2 minutes. The incubation was continued for 4 hours. The supernatants were discarded after centrifugation at 150 g for 10 minutes. 100 µl HCl-2-propanol (1:1) was added to the cell pellets and the pellets were shaken for 3 minutes. An ELISA reader referenced at 630 nm was used to obtain the $OD_{570}$ nm of each well.

2. CALCULATION

There were three assay and three control wells for each mouse. The Stimulation Index (SI) of each mouse was obtained by first deriving the average OD of the three parallel wells, then dividing the average value of the assay wells by that of the control wells.

3. RESULT

At 50 µg/kg/day, CMS017 was found to enhance T lymphocyte transformation, showing a statistically significant difference as compared with the saline control group ($P<0.05$), as shown in table below.

| The effect of CMS017 on T lymphocyte transformation | | | |
|---|---|---|---|
| Group | Dosage | N | X ± SD (stimulation index) |
| CMS 017 | 200 µg/kg/day | 12 | 2.65 ± 0.51 |
| CMS 017 | 50 µg/kg/day | 12 | 2.82 ± 0.41* |
| IL-2 | $3\times10^5$ IU/kg/d | 11 | 2.71 ± 0.35* |
| saline | 0.5 ml/day | 11 | 2.50 ± 0.23 |

*comparing to the saline control group $P \leq 0.05$

4. CONCLUSION

Peptides CMS017 was found to be able to enhance T lymphocyte transformation in vitro, inferring that CMS017 may have immuno-stimulating properties on animals.

5. REFERENCES

1. Principles of Pre-clinical Research of New Drugs, People's Republic of China. 1993, 7:134-135
2. Shuyun Xu, Rulian Bian, Xiu Chen. Methodology of pharmacological experiment. People's Health Publishing House. 1991, 1221-1234

Example 3

**Delivery of Peptides Through Genetically Engineered *Lactobacillus* Bacterial Species**

The following is provided as one exemplary method to deliver peptides of this invention to a host as described above. A DNA sequence that encodes a peptide selected from the group consisting of IVTNTT (CMS017) (SEQ ID NO:1) and functional derivatives thereof is synthesized by chemical means and this DNA sequence is inserted into an expression vector using standard techniques of genetic engineering familiar to those skilled in the art. The expression vector selected contains a constitutive promoter functional in *Lactobacilli*, a multiple cloning site for the introduction of DNA sequences in a specific 5' to 3' orientation as well as a selectable marker gene that confers resistance to an antibiotic (to aid in cloning procedures) and may comprise other sequences to assist in the production and/or secretion of the peptides, such as signal peptide sequences. An example of such a vector is provided by U.S. Pat. No. 5,529,908, to Palva, which is incorporated therein by reference in its entirety. Briefly, this patent discusses several known promoters that function in *Lactobacillus* species, as well as a method for discovering novel promoters in said bacteria, any of which may be operably linked to a nucleic acid encoding a peptide of the present invention to express the peptide in *Lactobacilli*. A nucleic acid encoding a signal peptide, such as peptides comprising of 16 to 35 mostly hydrophobic amino acids that are active in *Lactobacillus* lactis described in U.S. Pat. No. 5,529,908, cited above, is interposed between the promoter and the nucleic acid encoding the peptide of the present invention such that the nucleic acid encoding the signal peptide is in frame with the nucleic acid encoding the peptide of the present invention.

In addition to the coding sequence of the peptide, the DNA sequence synthesized may comprise sequences to aid in the ligation and cloning of said DNA into the expression vector. For example, restriction enzyme recognition sites that correspond to ones found in the multiple cloning site of the vector can be incorporated into the synthesized DNA at the 5' and 3' ends of the sequence, so that the sequence can be cloned in proper orientation within the vector. Both the vector and the synthesized DNA are digested with the particular restriction enzymes, then purified. Ligation reactions with the vector and the synthesized DNA are followed by transformation into a suitable strain of *E. Coli*. The transformed bacteria are plated on media containing the antibiotic to which the vector confers resistance. A colony of transformed bacteria is selected for growth cultures and plasmid preparation procedures; the presence of the synthesized DNA in the correct orientation is confirmed.

This expression vector is then transformed into a bacterial host cell of a *Lactobacillus* species, such as *L. acidophilus*. Transformed cells are selected for by virtue of the selectable marker found within the vector sequence and the secretion of the peptide may be verified by performing a western blot, performing gel electrophoresis of peptides present in the growth medium or other standard techniques. A transformed colony of bacteria is chosen and used to prepare large-scale cultures of the genetically engineered bacteria. A culture of the genetically engineered bacteria expressing the desired peptide is grown up and at least a portion thereof is administered to the alimentary canal, vagina, trachea or other area of the host organism in which the bacteria are able to replicate. If desired, the bacterial cultures can be treated in a variety of ways to produce a supplement for enteric consumption by the host. These treatments include lyophilization or other methods of preserving the bacteria, in addition to combining the bacteria with carrier agents, such as solutions, solvents, dispersion media, delay agents, emulsions and the like. The use of these agents to prepare supplements is well known in the art. For example, the bacteria can be used to make cultured milk products or other foodstuffs for human consumption, such that the organism expressing the peptide colonizes the gut of the host organism. A number of different methods for incorporating specific strains of lactic acid bacteria into foodstuffs such as yogurt, kimchee, cheese and butter are disclosed in U.S. Pat. No. 6,036,952, to Oh, which is incorporated herein by reference in its entirety. Upon consuming the bacteria through one of any number of routes, the engineered organisms can colonize the gut and allow the presentation and/or absorption of the peptides of this invention via the mucosal layer of the gut.

Example 4

**Delivery of Peptides Through a Genetically Engineered Form of *Bacillus subtilis***

The following is provided as another exemplary method to deliver peptides of this invention to a host as described above. A DNA sequence that encodes a peptide selected from the group consisting of IVTNTT (CMS017) (SEQ ID NO:1) and functional derivatives thereof is synthesized by chemical means and this DNA sequence is inserted into an expression vector via techniques of genetic engineering, all techniques being known in the art. The expression vector selected comprises a shuttle vector, such as pTZ18R (Pharmacia, Piscataway, N.J.), capable of being propagated in both *E. Coli* and *B. Subtilis* and containing an antibiotic resistance gene for selecting colonies of transformed bacteria. This vector can contain a constitutive promoter active in *B. subtilis*, such as a promoter derived from the Sac B gene of *B. subtilis* as well as a nucleotide sequence encoding a signal peptide active in *B. subtilis* that directs efficient export of expressed heterologous proteins from the bacterial cell. An example of such a vector is disclosed in U.S. Pat. No. 6,268,169, to Fahnestock, the disclosure of which is incorporated herein by reference in its entirety. Briefly, as detailed above, the DNA encoding a peptide of this invention will be synthesized with restriction enzymes sites and/or other sequences to facilitate cloning of the DNA through techniques familiar to those with skill in the art. After transformation into *E. Coli.*, plating, selection and propagation of the plasmid to create a plasmid stock, the plasmid is then be transformed into *B. subtilis* and transformants are selected by virtue of resistance to an antibiotic in the plating media.

Peptide production in and secretion from the genetically engineered *B. subtilis* is verified using techniques well known to those with skill in the art, such as radiolabeling of peptides for autoradiographic detection after SDS-PAGE analysis or Western blotting.

A culture of genetically engineered bacteria is grown up and at least a portion thereof is administered to the alimentary canal, vagina, trachea or other area of the host organism in which the bacteria are able to replicate.

Example 5

**Delivery of Peptides Through Genetically Engineered *Saccharomyces* Yeast Species**

The following is provided as another exemplary method to deliver peptides of this invention to a host as described above.

A DNA sequence that a peptide selected from the group consisting of IVTNTT (CMS017) (SEQ ID NO:1) and functional derivatives thereof is synthesized by chemical means and this DNA sequence is inserted into an expression vector via techniques of genetic engineering, all techniques being known in the art. The expression vector selected comprises a stably maintained yeast protein expression vector, comprising a constitutive yeast promoter such as pADH1, sites for replication of the vector in both yeast and *E. Coli*, a gene or genes that confer prototrophy to an auxotrophic yeast mutant for selection purposes, a multiple cloning site (MCS) and, if desired, sequences that code for a signal peptide. Vectors such as this are commercially available and well known in the art or can be readily constructed using standard techniques. After insertion of the synthesized DNA into the yeast vector, transformation into *E. Coli*, plating of transformed *E. Coli* onto selective media, selection of a transformed bacterial colony and preparation of plasmid DNA from a growth culture of bacteria from said colony, the vector is transformed into *Saccharomyces cerevisiae* via well-known techniques such as lithium acetate transformation or electroporation. The strain of *Saccharomyces cerevisiae* selected for transformation is a mutant auxotrophic strain that will require a gene on the plasmid in order to grow on minimal media plates. Transformed yeast colonies are isolated by plating the yeast on growth media lacking the gene provided on the vector. Only those yeast that have received the vector and its selective gene and are expressing that gene product will be able to grow into colonies on the minimal media. Verification of peptide secretion can be obtained by performing a Western blot, performing gel electrophoresis of peptides present in the growth medium or other standard techniques.

A transformed colony of yeast is chosen and used to prepare large scale cultures. A culture of the genetically engineered yeast expressing the desired peptide is grown up and at least a portion thereof is administered to the alimentary canal, vagina, trachea or other area of the host organism in which the bacteria are able to replicate. If desired, the yeast cultures can be treated in a variety of ways to produce a supplement for enteric consumption by the host. These treatments include lyophilization or other methods of preserving yeast, in addition to combining the bacteria with carrier agents, such as solutions, solvents, dispersion media, delay agents, emulsions and the like. The use of these agents to prepare supplements is well known in the art. In another embodiment, the transformed yeast are used in the creation of food products, such as fermented milk products like yogurt and kefir, by techniques known to those skilled in the art. As with live lactic acid bacterial cultures in these foodstuffs, the transformed yeast colonize the gut at least transiently and serve to present peptides to the host via the gut lumen.

Example 6

Targeting of a Peptide to a Particular Location

The following is provided as an exemplary method to selectively deliver a peptide of this invention to a particular compartment, organ, cell type or location within the body. In this case, an infection is treated by targeting a peptide selected from the group consisting of IVTNTT (CMS017) (SEQ ID NO:1) and functional derivatives thereof to tissues in the kidney of an individual. For example, IVTNTT (CMS017) (SEQ ID NO:1) is linked by covalent bonds via chemical reactions known in the art to low molecular weight (LMW) lysozyme, a commercially available protein moiety that concentrates specifically in renal tissue. Techniques for achieving conjugation of molecules to LMW lysozyme are documented (Folgert et al., Br. J. Pharmcology, 136:1107, 2002). General techniques for conjugating proteins or peptides to one another are also taught in the literature of the field (Fischer et al., Bioconj. Chem., 12:825, 2001). The newly created conjugated peptide sample is then purified away from chemical reagents used in the linking process by chromotography methods such as cation exchange FPLC and/or gradient centrifugation. Once purified, the conjugated peptide is administered to an individual in need of therapy for viral nephritis. For its antiviral activity, IVTNTT (CMS017) (SEQ ID NO:1) is preferentially targeted to renal tissue by virtue of the link between it and the LMW lysozyme, which is selectively concentrated in renal tissue by virtue of the affinity of the LMW lysozyme for the cells of the proximal tubules of the kidney. This preferential delivery allows a greater anti-nephritic effect compared to that of a molar equivalent amount of IVTNTT (CMS017) (SEQ ID NO:1) by itself. Inversely, it can reduce the amount of peptide drug required to achieve a certain level of anti-nephritic activity.

Example 7

Enhancing the Delivery of a Peptide to its Active Site

The following is presented as an exemplary method to increase the delivery of a neuroactive peptide to the brain. A peptide of the present invention that exerts its effects on receptors expressed by neurons of the brain is synthesized by chemical methods known to those with skill in the art. Alternatively, it can be expressed by an engineered microorganism and recovered from a culture of such organisms, as detailed in examples above. Once obtained in a purified form, the peptide is utilized in a series of organic chemical reactions to create a triglyceride ester conjugated moiety, attached to the peptide. The conjugated moiety consists of a quaternary substituted carbon center joined to the peptide of the invention through an amide bond with the terminal carboxyl carbon of the peptide. The other three groups attached to the quarternary carbon center consist of carbon ester linkages to 16 carbon fatty acid chains. The fatty acid chains themselves end in terminal dipeptide group, known as a peptide mask, which makes the chains more hydrophilic and targets them to the blood-brain barrier's endothelial cell membrane specifically. The procedure for this synthesis is explained at length in Patel et al., Bioconjugate Chem., 8(3):434, 1997, and utilizes common reagents and equipment familiar to those with skill in the art.

Once introduced into an individual at a peripheral location, the compound travels throughout the body via the circulatory system, interacting with the endothelial membrane of the blood brain barrier. Step-wise degradation of the dipeptide mask and the lipid chains during the transport of the molecule across the epithelial layer of the blood-brain barrier results in the release of the peptide of the invention into the brain compartment. There the peptide can interact with receptors on the surface of neurons to exert its effect on brain function. The time required for the drug to reach the blood brain barrier and be transported to the brain, with the concomitant degradation of the carrier moiety, alters the kinetics of the drug's activity, creating a more stable and longer lasting effect as compared to the intracerebro ventricular injection of the free peptide.

Example 8

Creating Peptide Formulations that are Resistant to Enzymatic Degradation

The following is provided as an exemplary method for creating a formulation of a biologically active peptide for oral administration that is resistant to the activity of proteases and peptidases found in and along the surface of the digestive tract. In this example, a peptide selected from the group consisting of IVTNTT (CMS017) (SEQ ID NO:1) and functional derivatives thereof is utilized in the making of a pharmaceutical formulation for oral administration to a patient. As described in Larionova et al. (Int. J. Pharma., 189:171, 1999), the peptide is used in the creation of microparticles with soluble starch and a protease inhibitor, aprotinin, that is a strong inhibitor of a variety of luminally secreted and brush border membrane-bound proteases. Briefly, soluble starch, the protease inhibitor aprotinin and the peptide of the invention are dissolved in an aqueous buffer. The ratios of soluble starch, aprotinin, and peptide are determined by experimental methods familiar to one with skill in the art; for example, Larionova et al. utilized in vitro simulated digestion assays to determine the ratios and preparation conditions most effective for the protein used in their study. The aqueous solution is emulsified under mechanical agitation in cyclohexane (1:3 ratio, v/v) containing 5% Span-80, a non-ionic surfactant. A terephthaloyl chloride solution in chloroform is added to the emulsion and stirring is continued 30 minutes, during which the starch molecules are cross-linked with the aprotinin and the peptide. The microparticles created in that process are washed with sequentially with cyclo-hexane, a 95% ethanol solution with 2% v/v Tween 85 detergent, 95% ethanol and water. The microparticles are resuspended in water and lyophilized. The lyophilized compound can be placed into gelatin capsules for oral delivery to the individual in need of treatment.

Once ingested, the compound is released as the gelatin capsule dissolved. The microparticles are broken down in the small intestine by the action of α amylase on the starch molecules, leading to the gradual release of aprotinin and the peptide of the invention. The concurrent release of the potent protease inhibitor aprotinin at the same time and location of the peptide decreases the enzymatic degradation of the peptide and increases the proportion of intact peptide available for absorption through the gut membrane.

While the present invention has been described using the aforementioned methods and data and the specific example of the CMS017 peptide (IVTNTT) (SEQ ID NO:1) in some cases, it is understood that this is an example only and should not be taken as limitation to the present invention. It should also be understood that IVTNTT (CMS017) (SEQ ID NO:1) represents one embodiment of the present invention and the same principle of the present invention can also apply to other functionally equivalent peptides that have been modified without affecting the biological function of IVTNTT (CMS017) (SEQ ID NO:1). For example, equivalents of IVTNTT (CMS017) (SEQ ID NO:1) include those that have conservative amino acid substitutions (i.e. one of the I, V, N or any T, replaced by another amino acid having a residue within the same biochemical type such as hydrophobic, hydrophilic, positive or negatively charged groups) Another example of an equivalent peptide to IVTNTT (CMS017) (SEQ ID NO:1) is a slightly longer peptide, such as one or two amino acids longer, that retains the same biological activities. Furthermore, although the disease or disorder described above for the medical application of IVTNTT (SEQ ID NO:1) specifically recite immunological disorders and/or viral infection, these medical applications are used as non-limiting examples only and should not be used to limit the scope of the claims. It is clear that there are other possible/intended use of IVTNTT and its functional derivatives, such as for use as a health food supplement to enhance or boost the immune system of a normal person or a patient with any infections. Any such uses also fall within the scope of the present invention.

---

---

What is claimed is:

1. A pure peptide consisting of the amino acid sequence of SEQ ID NO.1.

2. The peptide of claim 1, wherein said peptide reduces the symptoms of a viral disease.

3. The peptide of claim 2, wherein said viral disease is hepatitis B infection.

4. The peptide of claim 1, wherein said peptide has immuno-stimulating properties.

5. A pharmaceutical composition comprising a pure peptide consisting of the amino acid sequence of SEQ ID NO.1.

6. A method of making a pharmaceutical composition comprising providing a pure peptide consisting of the amino acid sequence of SEQ ID NO.1; and admixing said peptide with a pharmaceutically acceptable carrier.

7. A method of reducing the effects of a human disease comprising administering a pharmaceutically effective dose of a pure peptide consisting of the amino acid sequence of SEQ ID NO.1.

8. The method of claim 7, wherein said human suffers from a viral disease.

9. The method of claim 8, wherein said viral disease is hepatitis B infection.

10. A method of stimulating the immune system of an individual comprising administering a pharmaceutically effective dose of a pure peptide consisting of the amino acid sequence of SEQ ID NO.1.

11. The method of claim 10, wherein said peptide is administered with a food supplement.

12. The method of claim 11, wherein said peptide is administered as a nutritional formulation further comprising a pharmaceutically effective dose of a pure peptide consisting of the amino acid sequence of SEQ ID NO.1 admixed with a pharmaceutically or biologically acceptable carrier.

13. The method of claim 7, wherein said peptide is administered intravenously, intraarterially, intramuscularly, topically, intracutaneously, subcutaneously, intradermally, transdermally, orally or by inhalation.

14. The method of claim 10, wherein said peptide is administered intravenously, intraarterially, intramuscularly, topically, intracutaneously, subcutaneously, intradermally, transdermally, orally or by inhalation.

* * * * *